US010168216B2

(12) United States Patent
Kido

(10) Patent No.: US 10,168,216 B2
(45) Date of Patent: Jan. 1, 2019

(54) IMAGE INSPECTION DEVICE

(71) Applicant: Keyence Corporation, Osaka (JP)

(72) Inventor: Manabu Kido, Osaka (JP)

(73) Assignee: Keyence Corporation, Osaka (JP)

(*) Notice: Subject to any disclaimer, the term of this patent is extended or adjusted under 35 U.S.C. 154(b) by 0 days.

(21) Appl. No.: 15/925,802

(22) Filed: Mar. 20, 2018

(65) Prior Publication Data
US 2018/0328789 A1 Nov. 15, 2018

(30) Foreign Application Priority Data

May 9, 2017 (JP) ................. 2017-093361

(51) Int. Cl.
G01J 3/46 (2006.01)
G01J 3/50 (2006.01)
G06K 9/00 (2006.01)
G01N 21/88 (2006.01)
G06T 7/00 (2017.01)
G06K 9/34 (2006.01)
G06K 9/46 (2006.01)

(52) U.S. Cl.
CPC ............ G01J 3/502 (2013.01); G01N 21/88 (2013.01); G06K 9/00 (2013.01); G06K 9/34 (2013.01); G06K 9/46 (2013.01); G06T 7/00 (2013.01); G01J 2003/466 (2013.01)

(58) Field of Classification Search
CPC ........... G01N 21/88; G06T 7/00; G06T 15/00; G01S 3/786; H04N 13/02; G06K 9/00; G06K 9/46; G06K 9/34; G06K 9/62; G06K 9/68; G01K 3/502
See application file for complete search history.

(56) References Cited

U.S. PATENT DOCUMENTS

2014/0314302 A1* 10/2014 Minato ................. G06T 7/0004
382/141

FOREIGN PATENT DOCUMENTS

JP H09-126890 5/1997

OTHER PUBLICATIONS

U.S. Appl. No. 15/925,805, filed Mar. 20, 2018 (97 pages).
U.S. Appl. No. 15/925,804, filed Mar. 20, 2018 (75 pages).
U.S. Appl. No. 15/925,803, filed Mar. 20, 2018 (100 pages).
U.S. Appl. No. 15/925,801, filed Mar. 20, 2018 (74 pages).

* cited by examiner

Primary Examiner — Abdullahi Nur
(74) Attorney, Agent, or Firm — Kilyk & Bowersox, P.L.L.C.

(57) ABSTRACT

The invention reduces a variation of a result of image inspection by alleviating a burden on the user relating to designation of an extracted color. An image inspection device displays a color image of an inspection target object, receives designation of at least a foreground region, and extracts a foreground color and a background color as color information from the foreground region and a background region, respectively. The image inspection device calculates a distance between a color of each pixel of the color image and the foreground color in a color space, and generates a foreground distance image. Similarly, the image inspection device forms a background distance image. The image inspection device inspects the inspection target object using a foreground-background image created by combining the foreground distance image and the background distance image.

9 Claims, 21 Drawing Sheets

IMAGE INSPECTION DEVICE

CROSS-REFERENCE TO RELATED APPLICATIONS

The present application claims foreign priority based on Japanese Patent Application No. 2017-093361, filed May 9, 2017, the contents of which is incorporated herein by reference.

BACKGROUND OF THE INVENTION

1. Field of the Invention

The present invention relates to an image inspection device.

2. Description of Related Art

Image inspection devices that inspect an image obtained by capturing an image of a workpiece to determine whether a product (workpiece) has been produced as designed are extremely useful. A shape, a size, a color, and the like of the workpiece are inspected in such image inspection.

JP H09-126890 A proposes a color detecting apparatus which captures an image of an inspection target object such as a printed matter to acquire color information and executes color inspection with high accuracy.

In an image inspection device such as a color inspection device, a user selects a color to be extracted in a color image of a workpiece displayed on a display device, for example, by clicking the color. For example, in order to extract a contour of a specific part of the workpiece, color information of the specific part (foreground) and color information of surroundings (background) of the specific part are selected. The image inspection device converts the color image into a gray-scale image (gray image) using the foreground color information and the background color information as references. In this gray-scale image, a pixel closer to the foreground color information exhibits a lighter color, and a pixel closer to the background color information exhibits a darker color, and thus, it becomes easy to extract an edge of the specific part of the workpiece.

Meanwhile, when a color of a part of the workpiece with a specific color is not uniform, the user needs to select a plurality of colors which are close to the color of the part with the specific color. The same applies to the background. It is not easy for the user to define a color close to the foreground or a color close to the background, and thus, it is difficult to accurately extract all colors required for image inspection and to execute color gray-scale conversion.

SUMMARY OF THE INVENTION

Therefore, an object of the present invention is to reduce a variation of a result of image inspection by alleviating a burden on the user relating to designation of an extracted color.

For example, an image inspection device of the present invention includes: an acquisition unit which acquires a color image of an inspection target object, the color image including a plurality of spectral images; a display unit which displays the color image acquired by the acquisition unit; a region designation unit which receives designation of a plurality of foreground regions including a plurality of pixels in the color image displayed on the display unit; an extraction unit which extracts color information including a color distribution in each of the plurality of foreground regions designated by the region designation unit and color information including a color distribution in a background region distinguished from the plurality of foreground regions and registers the extracted color information as foreground colors for the plurality of foreground regions, respectively, and a background color for the background region; a foreground image generation unit which calculates a distance between a color of each pixel in the plurality of spectral images and each of the plurality of foreground colors on color space coordinates, generates a plurality of distance images having the distance as a pixel value, and generates a foreground distance image based on the plurality of generated distance images; a background image generation unit which calculates a distance between the color of each of the pixels in the plurality of spectral images and the background color on the color space coordinates, generates a distance image having the distance as a pixel value, and generates a background distance image based on the plurality of generated distance images; and an inspection unit which inspects the inspection target object using a foreground-background image which is a difference image between the foreground distance image and the background distance image.

According to the present invention, the burden on the user relating to the designation of the extracted color is alleviated, and the variation in the result of the image inspection is also reduced.

DETAILED DESCRIPTION OF PREFERRED EMBODIMENT

One embodiment of the present invention will be described below. Individual embodiments to be described below will be useful for understanding various concepts of the present invention such as superordinate concepts, intermediate concepts, and subordinate concepts. In addition, it should be understood that the technical scope of the present invention is defined by the scope of the claims and is not limited by the individual embodiments below.

Figure 1:
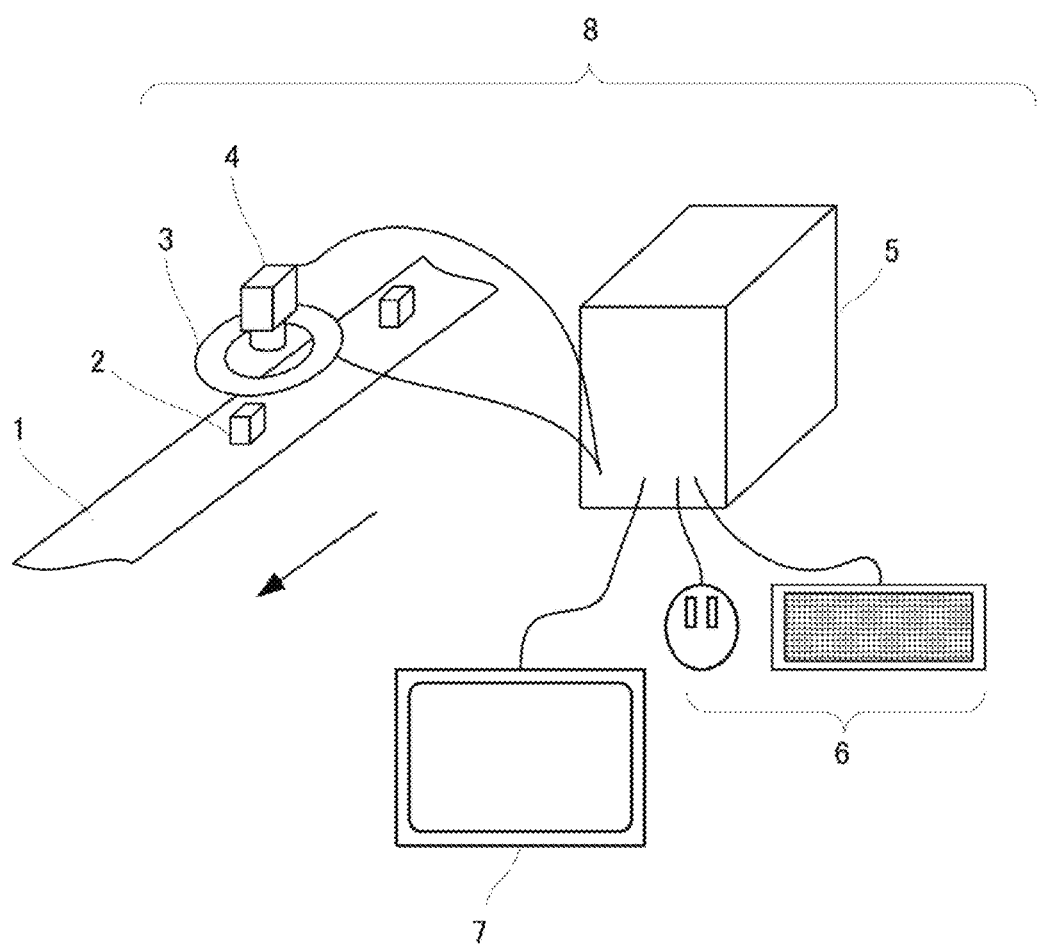
FIG. 1 is a view illustrating an image inspection device.

FIG. 1 is a view illustrating an example of a visual inspection system (image inspection device 8). A line 1 is a conveyor belt or the like for conveying a workpiece 2 which is an inspection target object. An illumination device 3 is an example of an illumination unit which includes a plurality of light emitting elements that generate inspection light (illumination beams) of mutually different wavelengths, and individually irradiates the target object with the illumination beam of each wavelength. A plurality of light emitting elements having the same wavelength may be provided in order to irradiate the workpiece 2 with the illumination beam simultaneously or sequentially from a plurality of directions. A camera 4 is an example of an imaging section for receiving light reflected from the inspection target object illuminated by the illumination beam and generating a luminance image (spectral image). An image processing device 5 includes an inspection unit which illuminates the inspection target object to be subjected to image inspection by sequentially turning on the light emitting elements at illumination intensity set for each wavelength, and executes the image inspection using a plurality of inspection images acquired by the imaging unit. A display unit 7 is a display device which displays a user interface for setting a control parameter relating to the inspection, the inspection images, and the like. An input unit 6 is a console, a pointing device, a keyboard, or the like, and is used to set the control parameter.

<Configuration of Illumination Device>

Figure 2A:
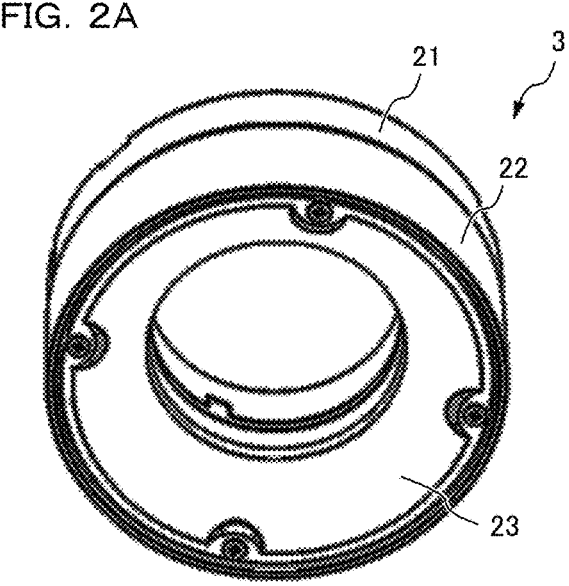
FIGS. 2A to 2D are views illustrating an illumination device.
Figure 2B:
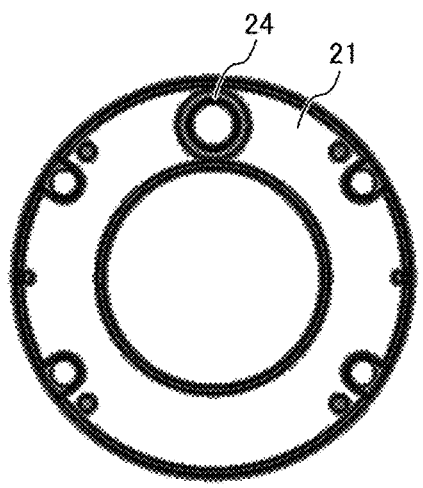
Figure 2C:
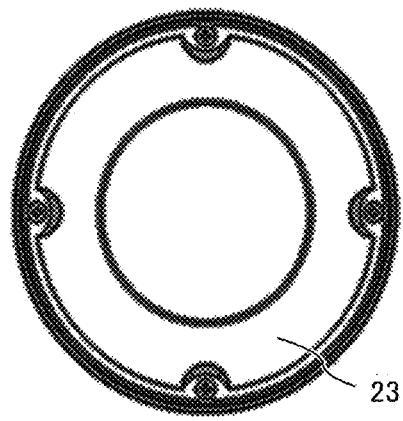
Figure 2D:
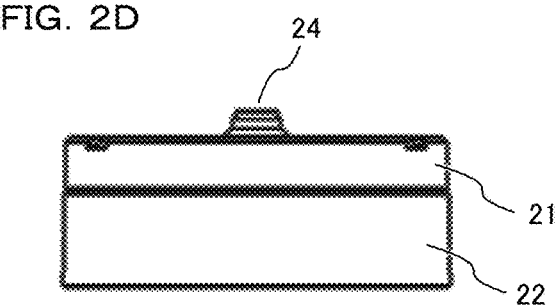

FIG. 2A is a perspective view of the illumination device 3. FIG. 2B is a top view of the illumination device 3. FIG. 2C is a bottom view of the illumination device 3. FIG. 2D is a side view of the illumination device 3. A casing of the illumination device 3 includes an upper case 21 and a lower case 22. A light diffusing member 23 which diffuses light output from each of a plurality of light sources (light emitting elements such as LEDs) is arranged at a lower part of the lower case 22. As illustrated in FIGS. 2A and 2C, the light diffusing member 23 also has an annular shape similarly to the upper case 21 and the lower case 22. As illustrated in FIGS. 2B and 2D, a connector 24 is provided on an upper surface of the upper case 21. A cable for communication between an illumination control board housed in the illumination device 3 and the image processing device 5 is connected to the connector 24. Some functions mounted on the illumination control board may be provided outside the illumination device 3 as an illumination controller. That is, the illumination controller may be interposed between the illumination device 3 and the image processing device 5.

Figure 3A:
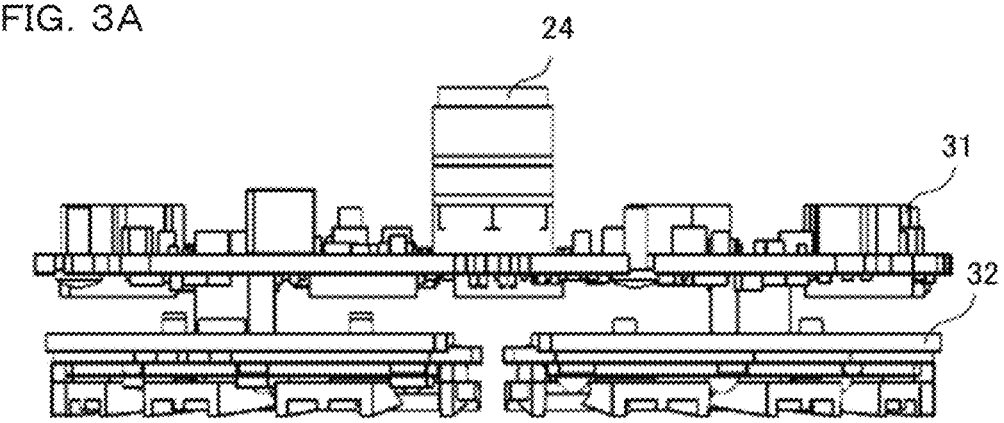
FIGS. 3A to 3E are views illustrating parts constituting the illumination device.
Figure 3B:
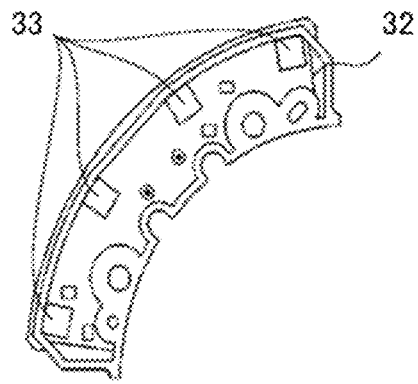
Figure 3C:
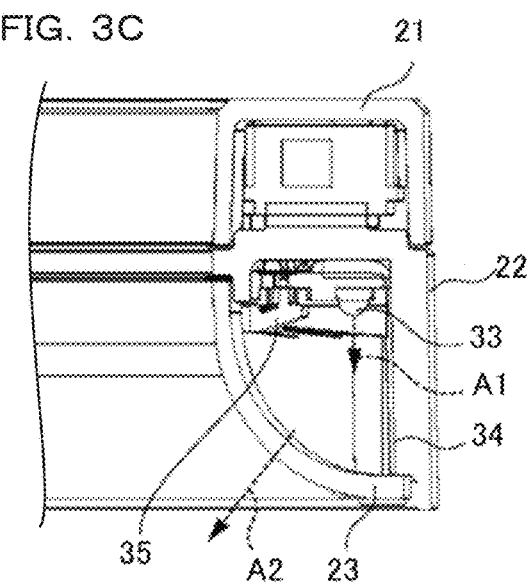
Figure 3D:
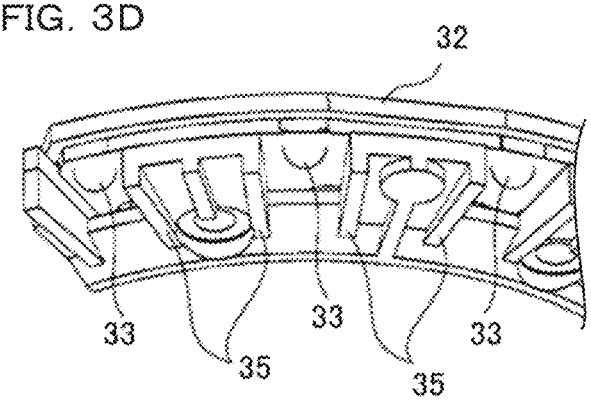
Figure 3E:
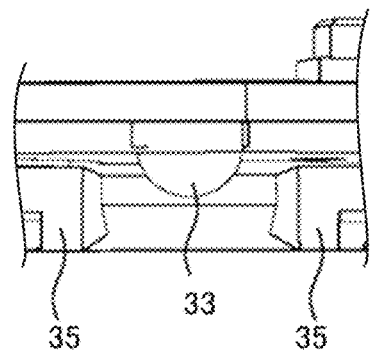

FIG. 3A is a side view illustrating a control board 31 and an LED board 32 housed in the illumination device 3. The control board 31 is an example of a second board on which a lighting control unit is mounted. The LED board 32 is an example of a first board on which the plurality of light sources are mounted. FIG. 3B is a top view of the LED board 32. FIG. 3C is an enlarged cross-sectional view of the vicinity of an LED 33 in the illumination device 3. FIG. 3D is a bottom view of the LED board 32. FIG. 3E is an enlarged side view of the vicinity of the LED 33 in the LED board 32.

The illumination control board and the connector 24 are arranged on the control board 31. The light emitting elements such as LEDs constituting a light source group are mounted on the LED board 32. As illustrated in FIG. 3B, four LED boards 32 are provided for irradiation of the illumination beam from four directions in the present embodiment. That is, one LED board 32 forms one illumination block. As the irradiation of the illumination beam from the four directions is possible, it is possible to acquire a photometric stereo image. That is, the illumination device 3 may be used not only for multi-spectral imaging (MSI) but also for photometric stereo. In a case where four LEDs 33 are arranged on the one LED board 32, the light source group is constituted by sixteen light emitting elements. Meanwhile, a larger number of light emitting elements may be provided. For example, eight LEDs 33 may be arranged on the one LED board 32, and wavelengths of light emitted by the eight LEDs 33 may be different from each other. As illustrated in FIGS. 3C, 3D, and 3E, a light shielding member 35 is arranged between the two adjacent LEDs 33 among the plurality of LEDs 33. When a large number of the LEDs 33 are closely arranged, illumination beams irradiated, respectively, from the two adjacent LEDs 33 may pass through the same region of the light diffusing member 23 in some cases. In this case, the surface of the workpiece 2 is irradiated with the illumination beams with the same amount of light from the same illumination direction in both of a case where one of the LEDs 33 is turned off and the other LED 33 is turned on and a case where the other LED 33 is turned off and the one LED 33 is turned on according to a lighting pattern. Then, it is difficult to generate the inspection images with high accuracy. Thus, a balance between uniformity of the amount of light and independence of the light source is obtained for the two adjacent LEDs 33 by arranging the light shielding member 35 between the two adjacent LEDs 33. As illustrated in FIG. 3C, a light emission direction A1 of the LED 33 does not coincide with a main illumination direction A2. Thus, the light emitted from the LED 33 is deflected toward the light diffusing member 23 by arranging a reflector 34. As a result, it is possible to efficiently irradiate the workpiece 2 with the light emitted from the LED 33. The emission direction A1 and a reflection direction of the reflector 34 are substantially orthogonal to each other in this example since a cross-sectional shape of the light diffusing member 23 forms an arc (FIG. 3C)) and an angle (central angle) of the arc is about 90 degrees. As the central angle is set large in this manner, it is easy to irradiate the surface of the workpiece 2 with substantially uniform parallel light even if the illumination device 3 is moved away from or close to the workpiece 2. According to the above drawings, the plurality of LEDs 33 are arranged on a certain circumference, but the plurality of LEDs 33 may be also arranged on another circumference having a different radius. As a result, the number of LEDs 33 for each wavelength increases so that it is possible to increase the amount of illumination light. In addition, the LEDs 33 for multi-spectral imaging may be arranged on a first circumference and the white LED may be arranged on a second circumference. A radius of the first circumference is different from a radius of the second circumference.

<Circuit Configuration of Illumination Device>

Figure 4:
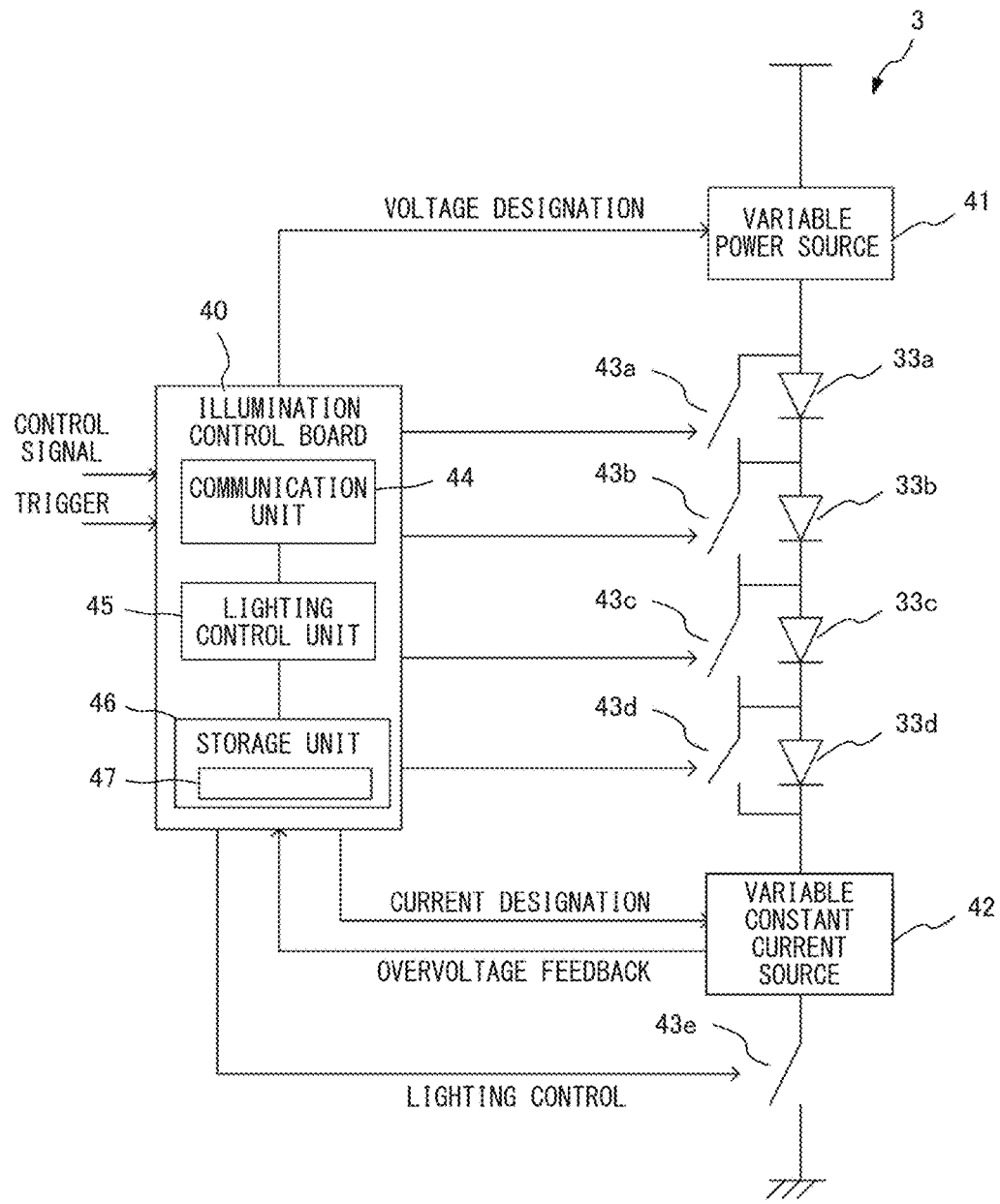
FIG. 4 is a diagram illustrating an electrical configuration of the illumination device.

FIG. 4 illustrates an example of a circuit configuration of the illumination device 3. In this example, one of the four illumination blocks constituting the light source group is illustrated. The four LEDs 33a to 33d are connected in series. A variable power source 41 with a variable voltage generates and outputs a voltage having a voltage value (for example, 2 V to 20 V) designated by an illumination control board 40. A variable constant current source 42 adjusts a current flowing in the illumination block so as to have a current value (for example, 0 A to 1 A) designated by the illumination control board 40. As such a current control system is employed, it is easy to realize dimming with high linearity. In addition, the variable constant current source 42 detects a value of a voltage applied to the variable constant current source 42 and performs feedback to the illumination control board 40, thereby protecting the variable constant current source 42 from an overvoltage. Switches 43a to 43d are connected in parallel to the LEDs 33a to 33d, respectively. A lighting control unit 45 of the illumination control board 40 can individually switch on and off of each of the LEDs 33a to 33d by individually opening and closing these switches 43a to 43d. As the switches 43a to 43d are connected in parallel to the LEDs 33a to 33d, respectively, in this manner, it is possible to perform the individual lighting by turning on any one of the LEDs 33a to 33d or turning on all of the LEDs 33a to 33d. This is useful for realizing various lighting patterns. The lighting control unit 45 executes the lighting control in the unit of one illumination block by switching on/off of a main switch 43e inserted between the variable constant current source 42 and a ground. A communication unit 44 receives a control signal to instruct a lighting pattern and a trigger signal to instruct start of lighting from an illumination control unit of the image processing device 5, and sends the signals to the lighting control unit 45. The lighting control unit 45 reads lighting pattern data 47 corresponding to the control signal from a storage unit 46 and controls the switches 43a to 43d according to the lighting pattern data 47. Eight switches 43 are provided when one illumination block is constituted by eight LEDs 33, and the eight switches 43 are controlled by the lighting control unit 45. For example, the eight LEDs 33 correspond to eight wavelengths from UV to IR2. UV represents a spectral image acquired by an illumination beam of an ultraviolet wavelength. B represents a spectral image acquired by an illumination beam of a blue wavelength. G represents a spectral image acquired by an illumination beam of a green wavelength. AM represents a spectral image acquired by an illumination beam of an amber wavelength. OR represents a spectral image acquired by an illumination beam of an orange wavelength. R represents a spectral image acquired by an illumination beam of a red wavelength. IR1 and IR2 represent spectral images acquired by illumination beams of infrared wavelengths. Here, the wavelength of IR1 is shorter than the wavelength of IR2.

<Functional Block>

Figure 5:
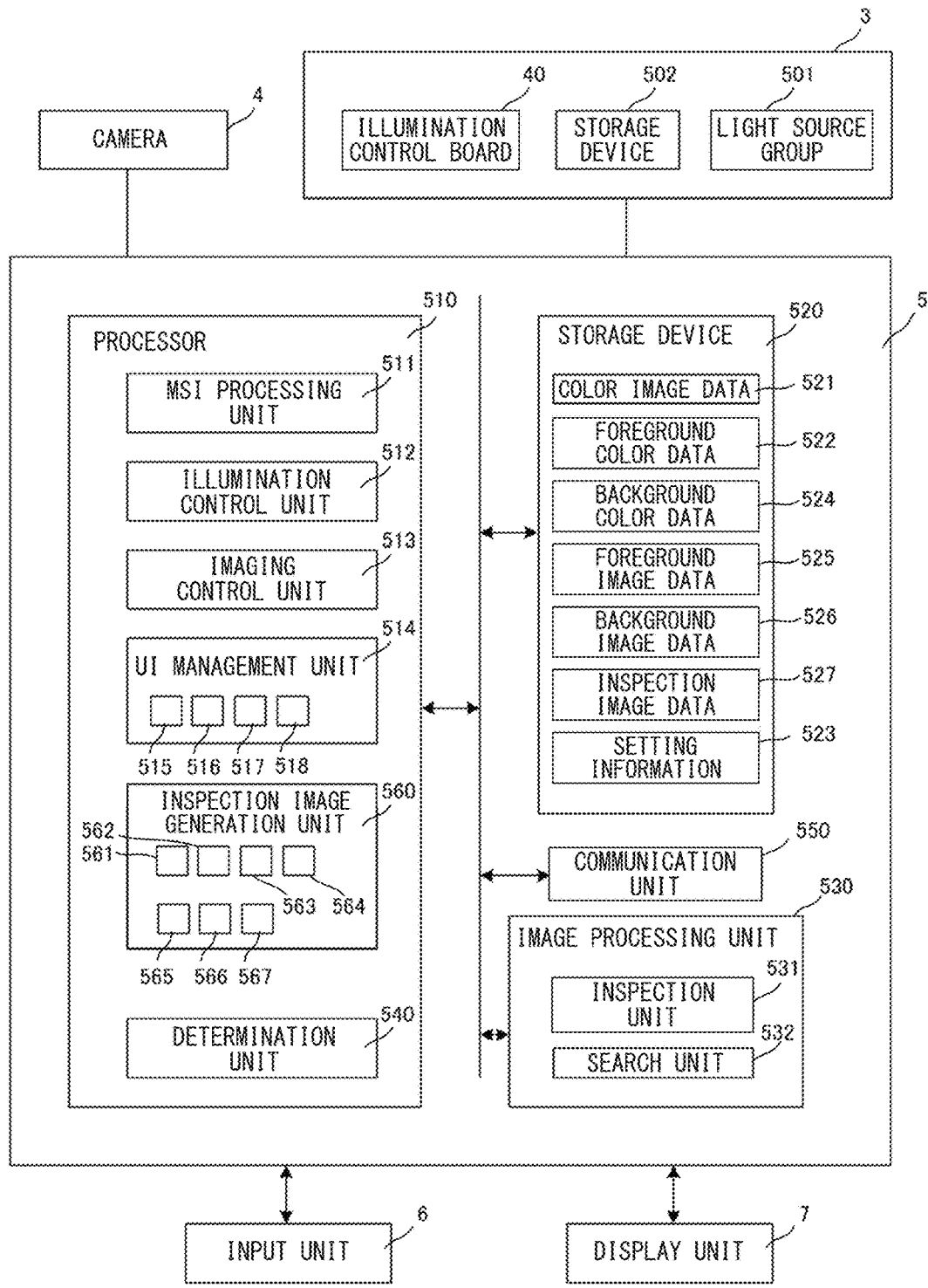
FIG. 5 is a diagram illustrating an image processing system.

FIG. 5 is a block diagram of an inspection device. In this example, the illumination device 3, the camera 4, and the image processing device 5 are housed in individual casings, respectively, but this is merely an example, and the integration thereof may be obtained as appropriate. The illumination device 3 is the illumination device that realizes the multi-spectral imaging, but may be used as an illumination section that illuminates an inspection target object according to a photometric stereo method. The illumination device 3 includes a light source group 501 and the illumination control board 40 that controls the light source group 501. As already illustrated in FIGS. 3A to 3E, one illumination block may be constituted by the plurality of light emitting elements, and the light source group 501 may be constituted by the plurality of illumination blocks. The number of illumination blocks is generally four, but may be three or more. This is because it is possible to generate an inspection image by the photometric stereo method if the workpiece 2 can be irradiated with illumination beams from three or more illumination directions. Each illumination block is provided with the plurality of light emitting elements (LEDs 33) that output illumination beams having different wavelengths, respectively. The plurality of light emitting elements may include the white LED. The white LED is not used for the multi-spectral imaging but can be used to create another inspection image and to create an image for movement correction of the workpiece 2. As illustrated in FIGS. 1 and 3A to 3E, an outer shape of the illumination device 3 may have a ring shape. In addition, the illumination device 3 may be constituted by a plurality of illumination units separated from each other. The illumination control board 40 controls a lighting timing and an illumination pattern (lighting pattern) of the light source group 501 according to a control command received from the image processing device 5. The workpiece 2 is irradiated with illumination beams of alternately selected wavelengths when acquiring the spectral image by the multi-spectral imaging, but may be irradiated simultaneously with the illumination beams of a plurality of wavelengths when a method other than the multi-spectral imaging is adopted. The illumination control board 40 has been described as being built in the illumination device 3, but may be built in the camera 4 or the image processing device 5, or may be housed in a casing independent therefrom.

A storage device 502 is built in the illumination device 3, and the lighting timing and the illumination pattern of the light source group 501 set by the user are stored therein. The illumination control board 40 can receive the trigger signal from the image processing device 5 and control the light source group 501 according to contents stored in the storage device 502. With this configuration, the image processing device 5 can control the illumination device 3 only by transmitting the trigger signal, and thus, it is possible to reduce the number of signal lines that connect the image processing device 5 and the illumination device 3, thereby improving the handling of cables.

The camera 4 is an example of the imaging section that receives light reflected from the inspection target object illuminated by the illumination device 3 and generates the luminance image, and executes imaging processing according to the control command from the image processing device 5. The camera 4 may create a luminance image of the workpiece 2 and transfer the created luminance image to the image processing device 5, or a luminance signal obtained from an imaging element of the camera 4 may be transferred to the image processing device 5 so that the image processing device 5 may generate a luminance image. Since the luminance image is based on the luminance signal, the luminance signal is also the luminance image in a broad sense. In addition, the camera 4 functions as the imaging unit that receives the light reflected from the target object for each of illumination beams of the respective wavelengths output from the illumination device 3 and generates the image (spectral image) of the target object.

The image processing device 5 is a type of computer, and includes a processor 510 such as a CPU and an ASIC, a storage device 520 such as a RAM, a ROM, and a portable storage medium, an image processing unit 530 such as an ASIC, and a communication unit 550 such as a network interface. The processor 510 performs setting of an inspection tool, adjustment of the control parameter, generation of the inspection image, and the like. In particular, an MSI processing unit 511 creates a gray image of the workpiece 2 from a plurality of luminance images (spectral images) acquired by the camera 4 or creates an inspection image from the gray image according to multi-spectral imaging (MSI). The gray image itself may be the inspection image. The MSI processing unit 511 may create one color image using the plurality of spectral images. An illumination control unit 512 controls the lighting pattern, an illumination switching timing, illumination intensity, and the like by transmitting the control command to the illumination control board 40. An imaging control unit 513 controls the camera 4 according to imaging conditions (an exposure time, a gain, and the like).

A UI management unit 514 displays a user interface (UI) for setting of the inspection tool, a UI for setting of a parameter required to generate the inspection image, and the like on the display unit 7, and sets the inspection tool and the parameter according to the information input from the input unit 6. The inspection tool may include a tool to measure a length of a specific characteristic (for example, a pin) provided in the workpiece 2, a tool to measure the area of the characteristic, a tool to measure a distance from a certain characteristic to another characteristic (for example, a pin interval) from one characteristic to another, a tool to measure the number of specific characteristics, a tool to inspect whether there is a flaw on a specific characteristic, and the like. In particular, the UI management unit 514 displays a UI for setting of a control parameter relating to color extraction on the display unit 7.

An image selection unit 515 reads image data of an image selected by the user through the UI from the storage device 520 and displays the image in an image display region inside the UI. For example, the image selection unit 515 acquires color image data 521 of the workpiece 2 to be subjected to color extraction from the storage device 520 through the UI.

A region designation unit 516 receives designation of an inspection region of the inspection tool and the like with respect to the displayed image from the user. In addition, the region designation unit 516 receives designation of an extraction region which is a region for extraction of a registered color from the displayed color image and which includes a plurality of pixels. The region designation unit 516 may receive selection of a shape (for example, a rectangle, a circle, an ellipse, or an arbitrary shape) of the extraction region and reflect a shape of a frame line indicating the extraction region to the UI. An extraction region of a foreground color may be referred to as a foreground region. An extraction region of a background color may be referred to as a background region. The foreground color is color information of a part (characteristic) to be subjected to image inspection. The part (characteristic) to be subjected to image inspection may be referred to as a foreground. A background is a part around the foreground and which is not subjected to image inspection. The background color is color information of the background. Designation of the background color extraction region may be automated.

An automatic region selection unit 517 selects the background color extraction region based on a position of the foreground color in a color space. For example, the automatic region selection unit 517 may select a color distant from the foreground color among the plurality of registered colors as the background color. Alternatively, when selection of one or more foreground colors is completed, the automatic region selection unit 517 may automatically select a color distant from all the selected foreground colors as the background color.

A gain adjustment unit 518 receives adjustment of the gain which is a coefficient to be used at the time of generating the inspection image.

An inspection image generation unit 560 generates an inspection image for image inspection from the color image of the inspection target object (such as the workpiece 2 which is conveyed on the line 1). The inspection image generation unit 560 has various functions. A color image is a spectral image group (multi-channel image) constituted by a plurality of spectral images.

An acquisition unit 561 acquires an image designated by the user through the image selection unit 515 from the storage device 520 and the camera 4. That is, the image selection unit 515 acquires image data through the acquisition unit 561.

An extraction unit 562 calculates the registered color such as the foreground color and the background color. For example, the extraction unit 562 extracts color information of the extraction region designated by the region designation unit 516 or the automatic region selection unit 517. The color information may include, for example, an average pixel, a variance-covariance matrix, and the number of pixels included in the extraction region, and the like. That is, the color information includes information indicating color distribution within a region.

A sorting unit 563 sorts the color information of the respective regions extracted by the extraction unit 562 into one of a foreground group and a background group according to the user's instruction. The foreground group is a group formed of the foreground color information (foreground color). The background group is a group formed of the background color information (background color). The sorting unit 563 stores the color information of the foreground color extracted by the extraction unit 562 in the storage device 520 as foreground color data 522. In addition, the sorting unit 563 stores the color information of the background color extracted by the extraction unit 562 in the storage device 520 as background color data 524.

A distance image generation unit 564 calculates a distance of a color of each pixel of the color image with respect to the registered color on color space coordinates, and generates a distance image by replacing a value of each pixel with the distance. For example, the distance image generation unit 564 generates nine distance images using one color image and nine foreground colors. In this manner, the distance image generation unit 564 has a distance calculating function. One color image is formed of a plurality of spectral images.

A foreground image generation unit 565 generates one foreground distance image (foreground image) based on a plurality of distance images obtained from a plurality of foreground colors. For example, the foreground image generation unit 565 compares distances of each pixel for the plurality of distance images, and decides a minimum distance as a value of the relevant pixel in the foreground distance image. In this manner, the foreground image generation unit 565 generates the foreground distance image by searching the minimum distance for all the pixels constituting the image. The foreground image generation unit 565 stores the foreground distance image in the storage device 520 as foreground image data 525.

A background image generation unit 566 generates one background distance image (background image) based on a distance image obtained from at least one background color. For example, the background image generation unit 566 compares distances of each pixel for a plurality of the distance images, and determines a minimum distance as a value of the relevant pixel in the background distance image. In this manner, the background image generation unit 566 generates the background distance image by searching the minimum distance for all the pixels constituting the image. There is only one distance image when there is only one background color, and thus, this distance image is directly set as the background distance image. The background image generation unit 566 stores the background distance image in the storage device 520 as background image data 526. The foreground image generation unit 565 and the background image generation unit 566 function as a minimum distance search unit.

A foreground-background image generation unit 567 generates a foreground-background image which is one type of inspection images based on the foreground distance image and the background distance image. The foreground-background image generation unit 567 may generate a difference image between the foreground distance image and the background distance image as the foreground-background image. That is, the foreground-background image generation unit 567 has a difference calculation function. The foreground-background image generation unit 567 stores the foreground-background image in the storage device 520 as inspection image data 527.

The inspection image generation unit 560 generates the inspection image by performing color gray conversion (color gray-scale conversion) on the color image based on the registered color. That is, inspection image generation unit 560 functions as a conversion unit that converts multi-dimensional color information of each pixel of the color image of the inspection target object into one-dimensional color information based on a distance between a color of each pixel of the color image of the inspection target object and the extracted color within the color space. The inspection image generation unit 560 may be entirely or partially included in the MSI processing unit 511.

The UI management unit 514 saves these control parameters set by the user in setting information 523. The UI management unit 514 may function as a setting unit that sets an illumination condition and an imaging condition or as a setting unit that sets the inspection tool.

The image processing unit 530 includes an inspection unit 531, which executes various types of measurement by applying the inspection tool to the inspection image, and the like. A search unit 532 searches for a characteristic set before image inspection or a characteristic dynamically set during the image inspection within a search region SW arranged in the inspection image, and obtains a position of the found characteristic. The inspection unit 531 corrects a position of the inspection region (measurement region) according to the position of the found characteristic. The function of the image processing unit 530 may be implemented on the processor 510. Alternatively, the function of the processor 510 may be implemented on the image processing unit 530. In addition, the processor 510 and the processor 510 may implement a single function or a plurality of functions in cooperation with each other.

A determination unit 540 functions as a determination section for determining whether the workpiece 2 is non-defective/defective using the inspection image. For example, the determination unit 540 receives a result of the inspection performed using the inspection image in the image processing unit 530 and determines whether the inspection result satisfies a non-defective product condition (the tolerance or the like).

The storage device 520 stores the color image data 521 which is data of the color image acquired by the camera 4, the inspection image data 527 which is image data of the inspection image, and setting information 523 holding various control parameters. In addition, the storage device 520 also stores various types of setting data, a program code for generating the user interface, and the like. The storage device 520 may also store and hold the inspection image generated from the gray image and the like.

Figure 14:
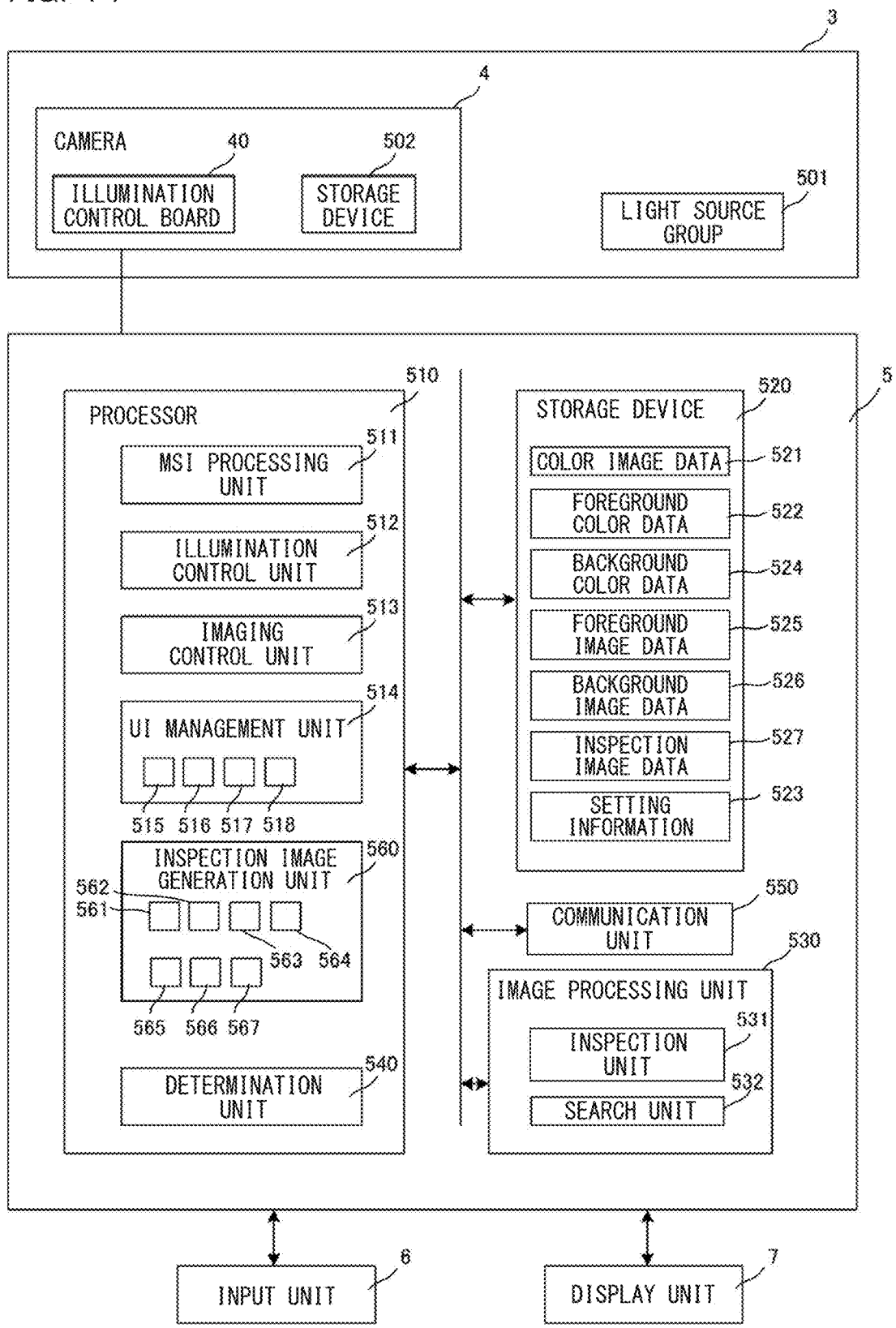
FIG. 14 is a diagram illustrating an image processing system.
Figure 15:
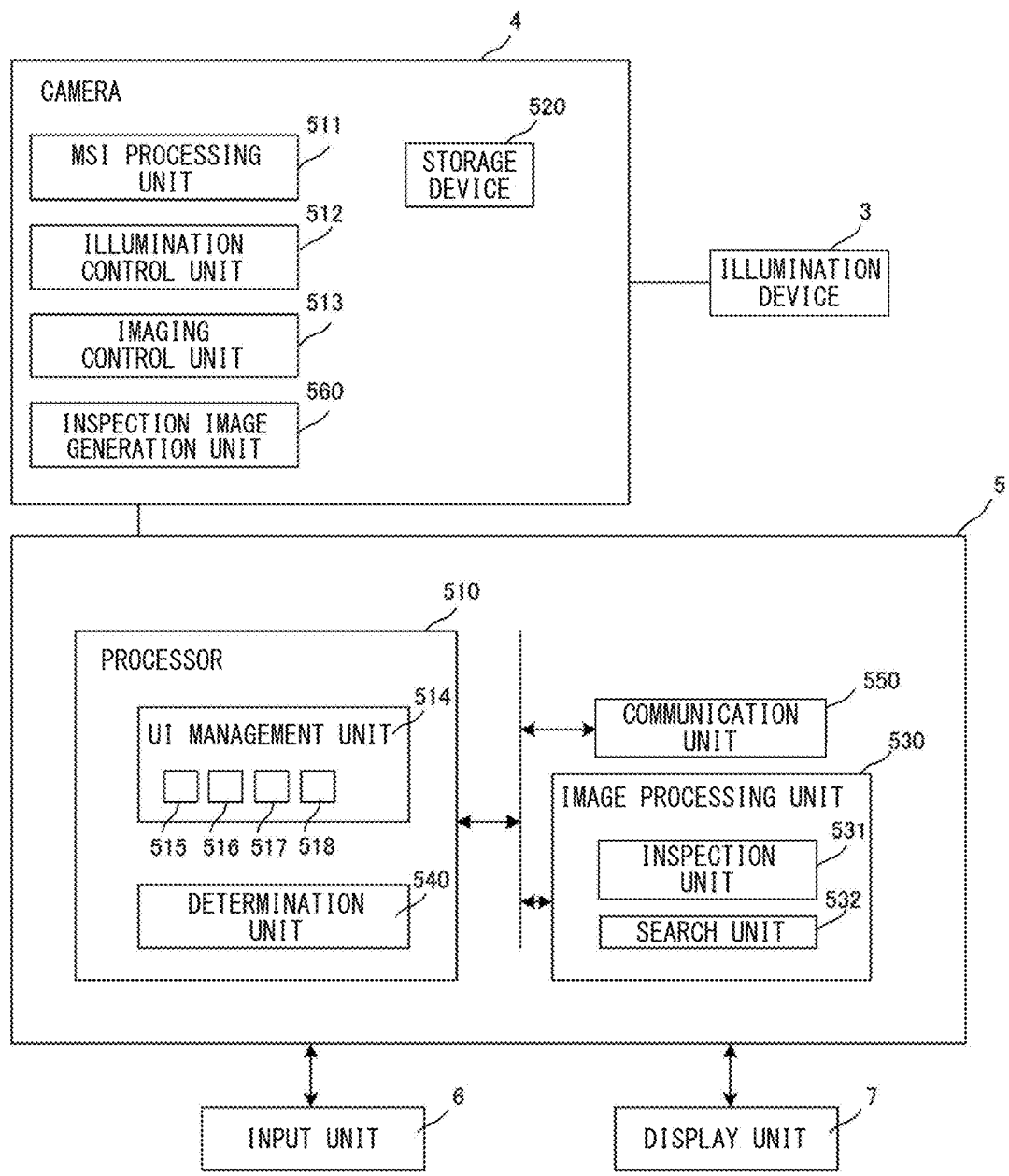
FIG. 15 is a diagram illustrating an image processing system.
Figure 16:
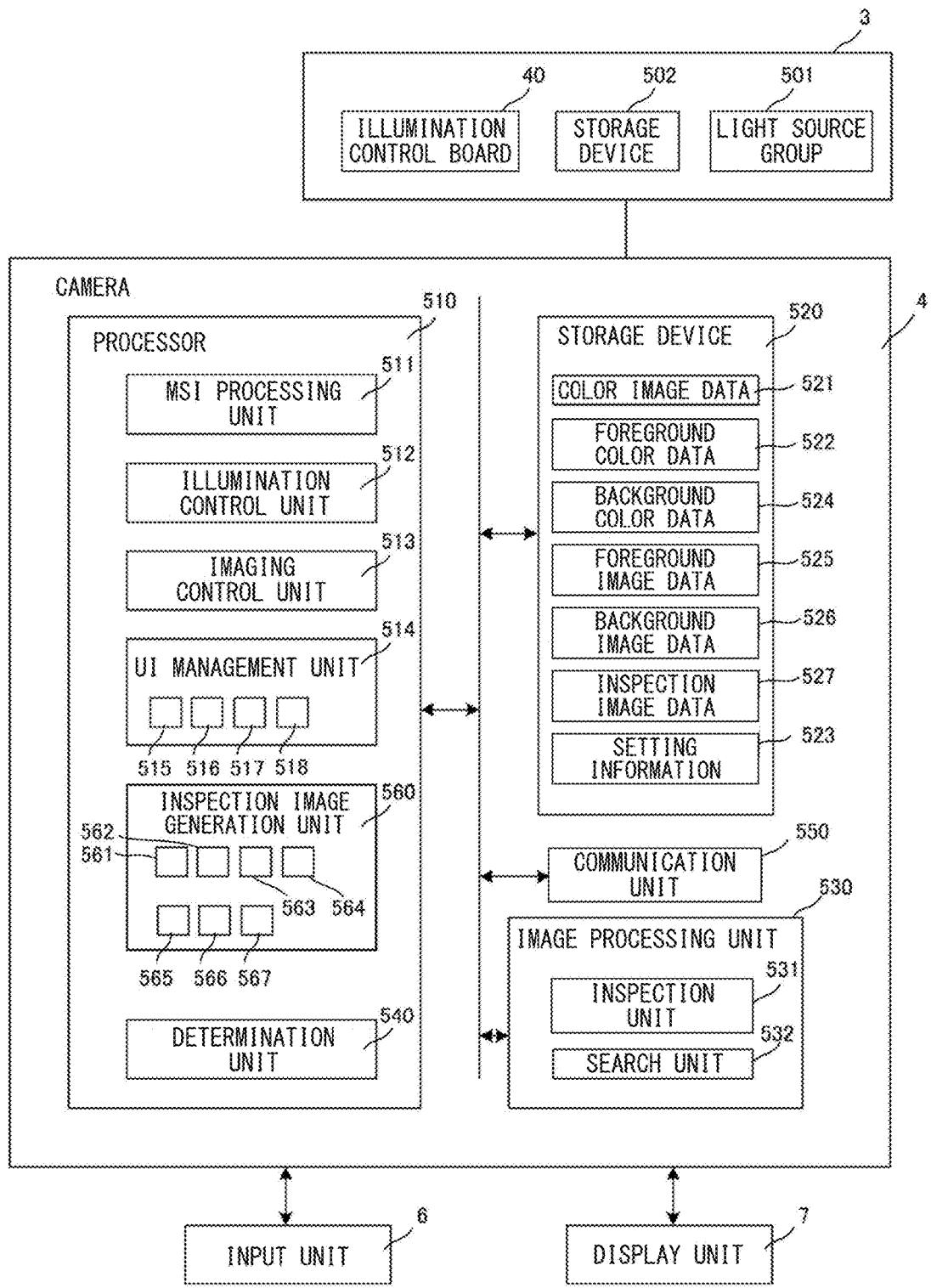
FIG. 16 is a diagram illustrating an image processing system.

FIGS. 14 to 16 are diagrams illustrating another configuration example of the image processing device of the present invention. FIG. 14 is the diagram illustrating an example in which the illumination device 3 and the camera 4 are integrated, and the illumination control board 40 configured to control the illumination device 3 is provided in the camera 4. Since the illumination device 3 and the camera 4 are integrally provided in this configuration, it is not necessary to perform positioning at the time of installing the illumination device 3 and the camera 4. In addition, the illumination control board 40 configured to control the light source group 501 and the storage device 502 are unnecessary on the illumination device 3 side, and the general-purpose illumination device 3 that does not include the illumination control board 40 and the storage device 502 can also be used. The user can remove the illumination device 3 connected to the camera 4 and replace the illumination device 3 with another type of illumination device. For example, it is possible to appropriately select other types of illumination devices, such as a ring illumination that emits only white light, instead of the illumination device 3 used for the multi-spectral imaging in the present invention. It is preferable that the camera 4 recognize the type of the connected illumination device 3 and reflect the type on the setting user interface. Accordingly, the user can perform the illumination setting on the user interface corresponding to an item that can be set in the connected illumination device 3. A method in which the illumination device 3 stores illumination type information and the camera 4 refers to the information is conceivable as a method of recognition. In addition, the illumination control unit 512 and the imaging control unit 513 included in the image processing device 5 may be provided inside the camera 4, and control of an imaging and illumination system may be executed independently from the image processing device 5.

FIG. 15 illustrates a configuration example in which some functions of the image processing device 5 are provided on the camera 4 side. The camera 4 includes the storage device 520 that stores the spectral image data 521, the foreground color data 522, the background color data 524, the foreground image data 525, the background image data 526, the inspection image data 527, and the setting information 523. Inside the camera 4, the MSI processing unit 511 or the inspection image generation unit 560 creates the foreground image data 522 using the spectral image data 521 and the foreground color data 522. Inside the camera 4, the MSI processing unit 511 or the inspection image generation unit 560 creates the background image data 526 using the spectral image data 521 and the background color data 524. Further, the inspection image generation unit 560 creates the inspection image data 527 using the foreground image data 522 and the background image data 526. The illumination device 3 is controlled by the illumination control unit 512 of the camera 4. At the time of inspection setting, the camera 4 transmits the spectral image data 521, the foreground color data 522, the background color data 524, the foreground image data 525, the background image data 526, and the like captured at each wavelength to the image processing device 4 to the image processing device 5. At the time of setting, the image processing device 5 acquires the spectral image data 521 from the camera 4 and displays the acquired data on the display unit 7, so that the user can confirm the illumination intensity of each wavelength and whether the spectral image data 521 of each wavelength is necessary for inspection. On the other hand, at the time of inspection operation, the inspection image data 527 to be inspected may be transmitted to the image processing device 5 without transmitting the spectral image data 521 from the camera 4 to the image processing device 5. As the camera 4 is caused to have some functions of the image processing device 5 in this manner, a communication load between the camera 4 and the image processing device 5 is reduced, and the speed of processing increases due to distributed processing.

FIG. 16 is the configuration example in which all functions of the image processing device 5 are incorporated in the camera 4. It is sufficient for the user to install only the camera 4 and the illumination device 3, and thus, little time and effort is required at the time of installation. For example, this configuration may be advantageous when the camera 4 is allowed to have a large size and advanced image processing is unnecessary.

<Multi-Spectral Imaging>

In the multi-spectral imaging, the workpiece 2 is irradiated sequentially with illumination beams having different lighting colors (wavelengths) one by one, and an image for each wavelength is acquired. Strictly speaking, wavelengths may not be different from each other, and it is sufficient that spectrums are different from each other. For example, eight images (spectral images) are acquired in the case of irradiation with illumination beams of eight types of wavelengths. When there are four illumination blocks, the four illumination blocks are turned on at the same time. That is, since the four LEDs 33 of the same wavelength are simultaneously turned on, the workpiece 2 is irradiated with the illumination beams of the same wavelength from four directions. For example, the eight types of wavelengths are eight narrow-band wavelengths from an ultraviolet wavelength to a near-infrared wavelength. The narrow-band wavelength refers to a wavelength narrower than a width of a wavelength (wide-band wavelength) of light emitted by the white LED. For example, a width of a wavelength of light emitted by a blue LED is much narrower than the wavelength width of the light emitted by the white LED, and thus, the wavelength of the light emitted by the blue LED is the narrow-band wavelength. In the image inspection, there may be image inspection that does not require all of the eight spectral images. In this case, the workpiece 2 is irradiated with only an illumination beam of a necessary wavelength. In general, it is unlikely that the eight images are directly used for image inspection. One gray image is created from the eight images (color gray-scale conversion), and this gray image (color gray-scale image) is used for the image inspection. The color gray-scale conversion is sometimes called color-gray conversion. For example, binarization processing is executed on the color gray-scale image, edge detection processing is executed, or blob processing is executed so that whether a position, a size (a length or area) and a color of a characteristic (for example, a pin) in the workpiece 2 fall within tolerance ranges, respectively, are inspected.

The spectral image may be generated by white light emitted by the white LED.

Figure 6:
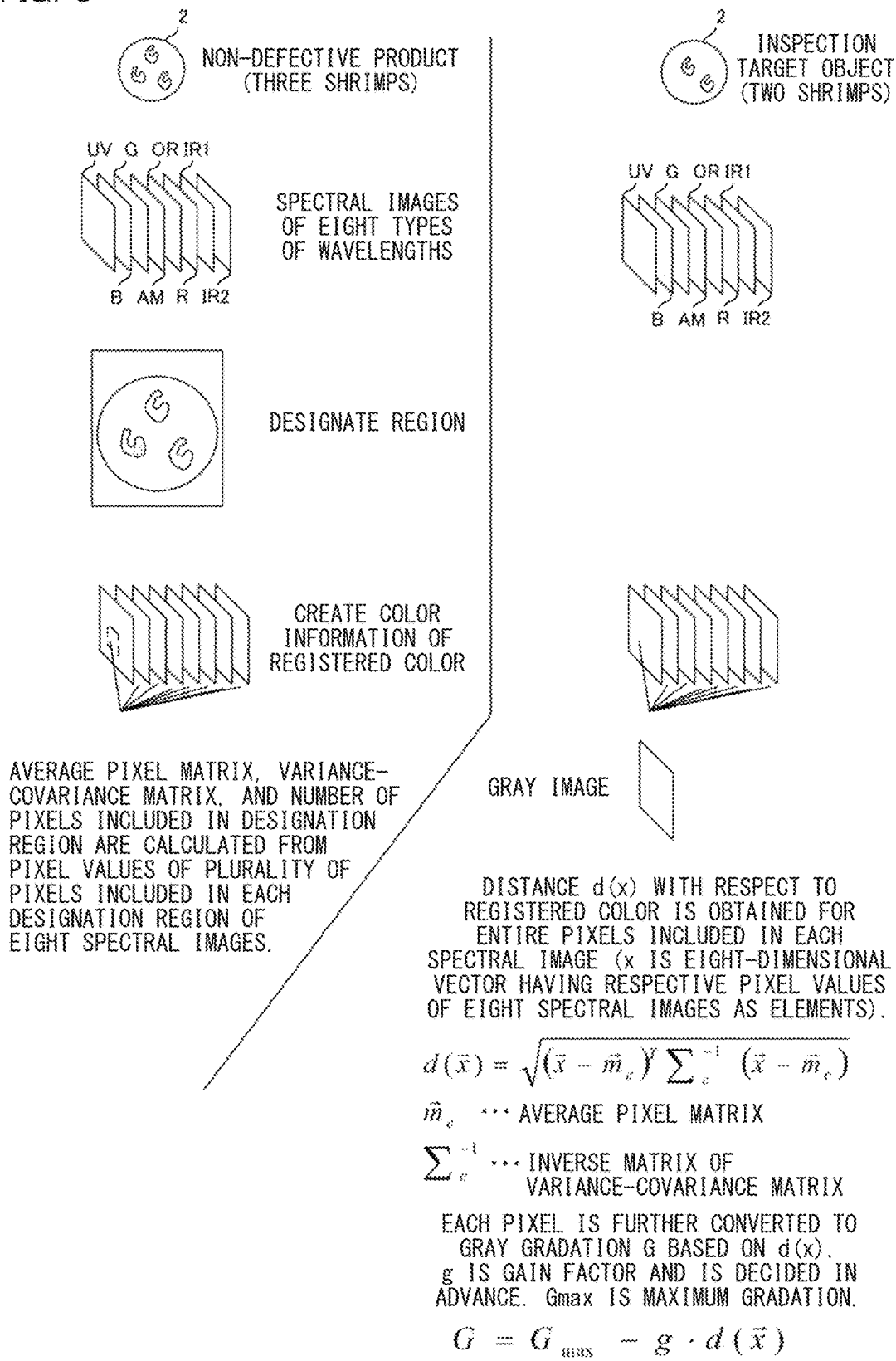
FIG. 6 is a view illustrating a principle of color gray-scale conversion in multi-spectral imaging.

An example of the color gray-scale conversion will be described with reference to FIG. 6. When creating the gray image of the workpiece 2 which is the inspection target object, a registered color of a non-defective product (model) is required. This is because the gray image is created by converting the eight spectral images using color information of the registered color as a reference.

First, in a setting mode, the color information of the registered color is extracted from an image region (designation region) designated by the user in the eight spectral images acquired from the non-defective product. For example, when the non-defective product is an instant food (for example, Chinese noodle) and the number of certain ingredients (for example, shrimps) is counted by image inspection, the user displays an image of the non-defective product and designates a rectangular designation region including the ingredient in the non-defective product image, and the color information of the registered color is extracted from pixels included in the designation region. The color information of the registered color includes an average pixel matrix, a variance-covariance matrix, and the number of the pixels included in the designation region. The color information may be extracted by a so-called dropper tool. An UI of the dropper tool may be implemented on the region designation unit 516.

Next, eight spectral images are acquired for the workpiece 2 as the inspection target object in the inspection mode. A distance $d(x)$ with respect to the registered color is obtained for all pixels included in each spectral image (x is an eight-dimensional vector having the respective pixel values of the eight spectral images as elements). Further, a product is obtained by multiplying the distance $d(x)$ by a predetermined gain g, an offset a is added if necessary, and a difference G obtained by subtracting the product from a maximum gradation Gmax that each pixel can take becomes a gray gradation of a pixel x of interest. This is expressed as $G = Gmax - (g \cdot d(x) + a)$.

When there are a plurality of registered colors, a plurality of gray images may be created using each registered color as a reference, or a single gray image may be created.

In addition, the above-described color-gray conversion can be adopted when converting a color image such as an RGB image to a gray image. Even in this case, color information of each pixel is converted into gray-scale information using a certain registered color (a color designated by the user) as a reference, and a gray image is generated. In addition, the variance-covariance matrix may be decomposed into a matrix indicating brightness and a matrix indicating chromaticity. In addition, the brightness matrix may be multiplied by a brightness scale (a coefficient Sy) for adjusting the brightness matrix. Similarly, the chromaticity matrix may be multiplied by a chromaticity scale (a coefficient Sz) for adjusting the chromaticity matrix. These scales may be changed by adjusting the distribution of the extracted color.

<Color Extraction (Designation of Registered Color)>

An image generated by the MSI is a multi-channel image. That is, each pixel is represented by three-dimensional elements such as RGB, or expressed by eight-dimensional elements from UV to IR2. In general, an image that can be handled by an image inspection tool of the image inspection device 8 is a one-dimensional gray-scale image (gray image). This means that color gray-scale conversion is required. In the color gray-scale conversion, Mahalanobis distance with respect to a registered color designated by the user is obtained. Therefore, a gray-scale image differs depending on which color the user selects as the registered color, and a variation in image inspection occurs. In particular, when the color of the part to be measured on the surface of the workpiece 2 is not uniform and includes many colors, this problem becomes obvious. This problem can be solved by holding color information of all pixels constituting the part. However, not only a large amount of memory is required to hold and calculate the entire color information, but also a great computing capacity is required. Therefore, several colors need to be selected as registered colors.

Meanwhile, even when the part has a plurality of colors, the respective colors are similar to each other in many cases. This is because a cause of occurrence of the plurality of colors lies in coating unevenness and pigment unevenness, and the like. In addition, there is a case where a plurality of colors actually exists although it appears to be a single color to human eyes. Accordingly, when a registered color is extracted only by designating one pixel of a specific part, the variation in image inspection occurs for each user. Therefore, in the present embodiment, the plurality of pieces of color information constituting the part to be measured are extracted from the designation region, thereby reducing the variations in image inspection. In addition, it is possible to accurately separate the foreground from the background by grouping the color information into the foreground group and the background group as necessary.

User Interface

Figure 7:
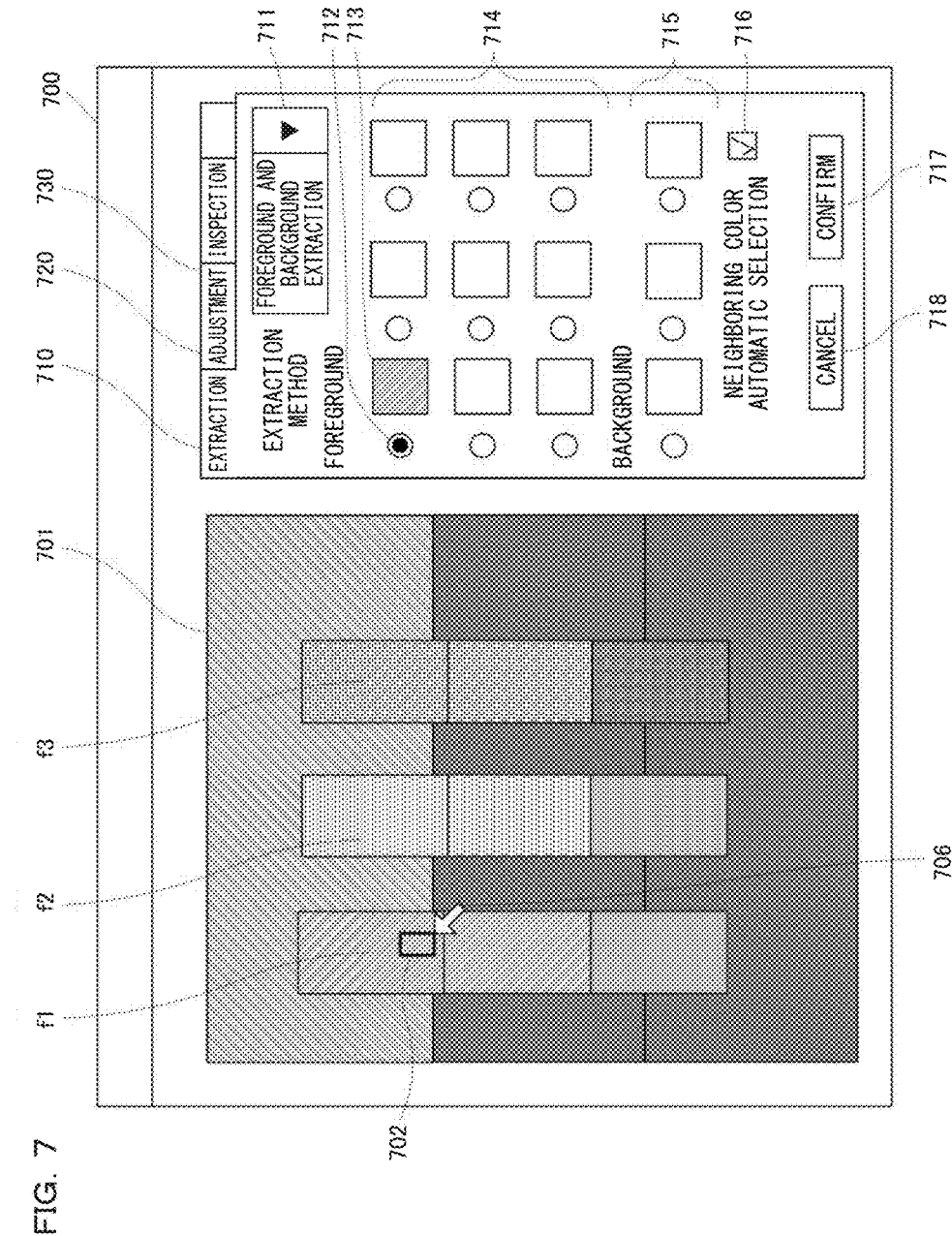
FIG. 7 is a view illustrating a UI that assists designation of an extracted color.
Figure 8:
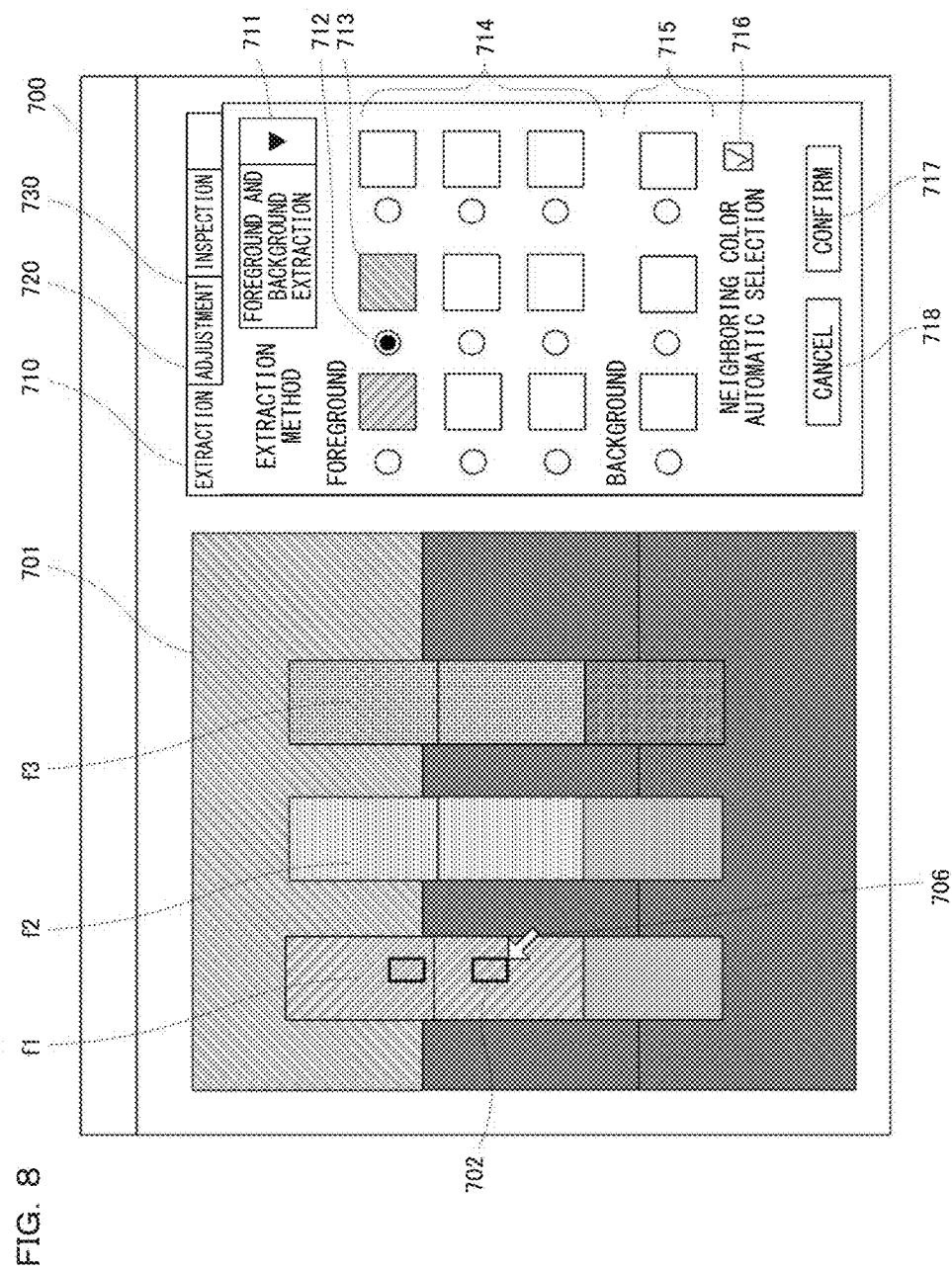
FIG. 8 is a view illustrating a UI that assists designation of an extracted color.
Figure 9:
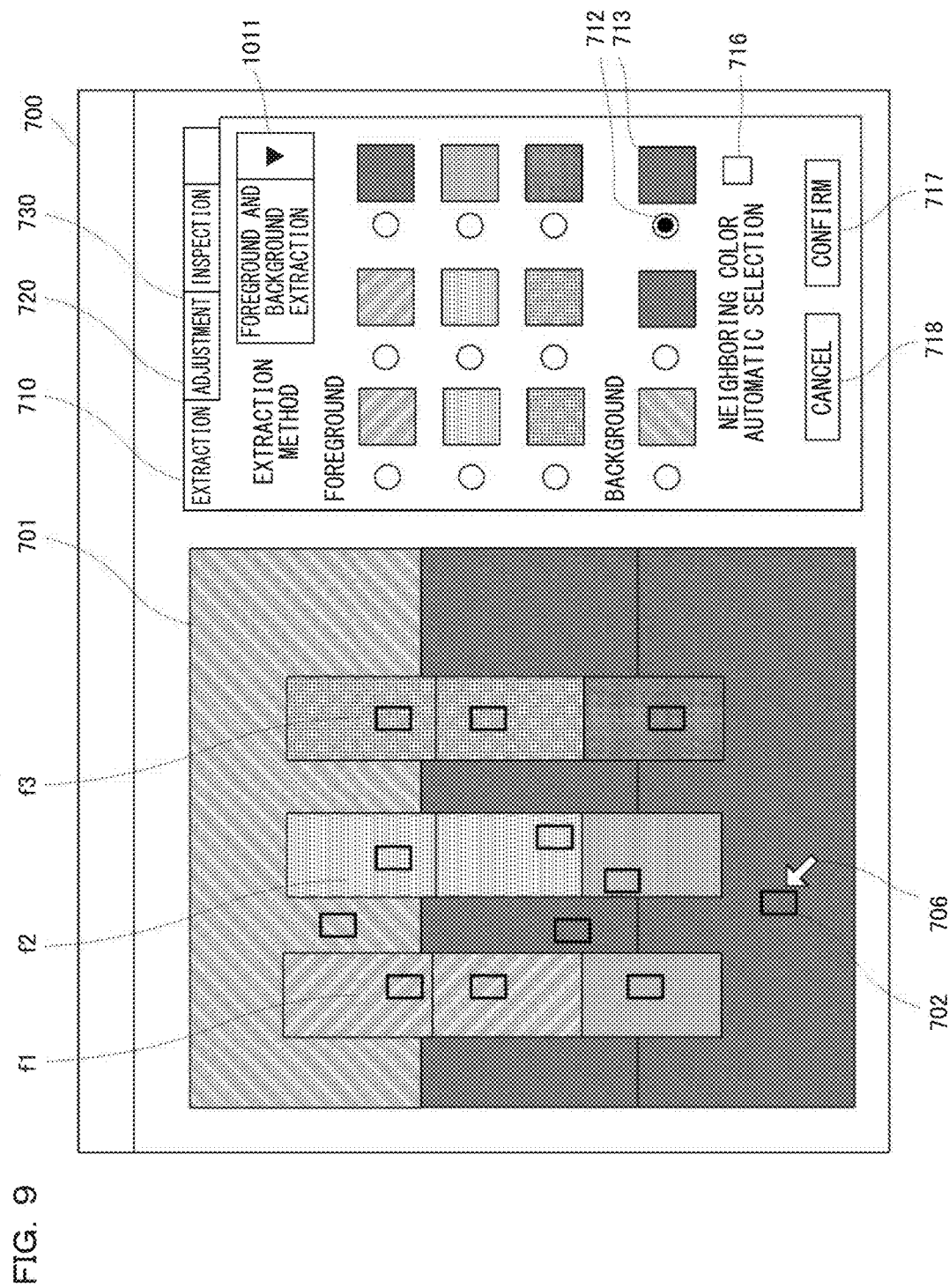
FIG. 9 is a view illustrating a UI that assists designation of an extracted color.

FIGS. 7, 8, and 9 illustrate an UI 700 configured to perform extraction of a registered color. The UI 700 has an image display region 701 and setting tabs configured to perform various types of setting. In the image display region 701, a color image selected by the image selection unit 515 and acquired by the acquisition unit 561 is displayed by the UI management unit 514. Although not illustrated, the UI 700 may be provided with a pull-down menu or the like for selection of an image to be displayed in the image display region 701. Such a pull-down menu is a UI configured to designate a color image stored in the storage device 520, a color image acquired by the camera 4, and the like. An image, which is not registered in the pull-down menu, may be allowed to be designated by selecting "reference" in the pull-down menu. The image selection unit 515 displays the image selected by the pull-down menu in the image display region 701. In FIG. 7, an image of the workpiece 2 including three cables f1, f2, and f3 having mutually different colors is displayed in the image display region 701. For example, the color of the cable f1 is a color recognized as red to human eyes. The color of the cable f2 is a color recognized as green to human eyes. The color of the cable f3 is a color recognized as blue to human eyes. In addition, the color of each cable has color unevenness, and, strictly speaking, is not the identical color.

An extraction tab 710 is a UI for extraction of a registered color. The user operates a pull-down menu 711 with a pointer 706 and selects "foreground and background extraction" as a color extraction method. The foreground and background extraction is to extract a plurality of colors (foreground colors) of a characteristic to be measured (foreground) and a plurality of colors (background colors) of the surroundings to be measured (background) from the color image of the workpiece 2 as registered colors, respectively. Color information of the plurality of foreground colors forms the foreground group. Color information of the plurality of background colors forms the background group. A foreground group display region 714 is a region to display registered colors that belong to the foreground group. A background group display region 715 is a region to display registered colors (foreground colors) that belong to the background group. Each of the foreground group display region 714 and the background group display region 715 includes a plurality of radio buttons 712 and a plurality of registered color display regions 713. The radio button 712 is a button configured to designate which color among the plurality of foreground colors and the plurality of background colors is to be registered. In this example, there are nine radio buttons 712 in the foreground group display region 714, and thus, it is possible to register a maximum of nine foreground colors. In addition, there are three radio buttons 712 in the background group display region 715, and thus, it is possible to register a maximum of three background colors. The number of radio buttons 712 is merely an example. As an extreme example, the number of radio buttons 712 for the background group may be one. The user selects the radio button 712 corresponding to the color to be desirably registered using the pointer 706, and then, moves the pointer 706 to a position of a color to be desirably registered in the image of the workpiece 2. The user may designate an extraction region 702 by dragging the pointer 706. More specifically, the region designation unit 516 detects a start position and an end position of dragging of the pointer 706, and draws the rectangular extraction region 702 whose diagonal is a line connecting the start position and the end position. In this manner, the region designation unit 516 receives the designation of the extraction region 702. The extraction unit 562 calculates color information of a plurality of pixels existing in the extraction region 702 and displays a representative color (average color) of color distribution inside the extraction region 702 in the registered color display region 713. The colors of the plurality of pixels in the extraction region 702 have a certain distribution as described with respect to MSI. Accordingly, the representative color may be a center coordinate (average color) of the color distribution in the extraction region 702. In this manner, the variation of the registered color is reduced.

As illustrated in FIG. 8, the user clicks the second radio button 712 to designate a second registered color that belongs to the foreground group. Further, the user moves the pointer 706 to the position of the color to be desirably registered in the image of the workpiece 2, and further, designates the second extraction region 702 by dragging the pointer 706. The extraction unit 562 calculates a representative color of the second extraction region 702 and displays this second representative color in the second registered color display region 713. The user repeats this work for the foreground group and the background group as many times as the user desires.

FIG. 9 illustrates that nine foreground colors and three background colors are extracted as registered colors in the UI 700. As described above, the color information of the registered color includes the average pixel, the variance-covariance matrix, and the number of pixels in the extraction region 702, and is stored in the storage device 520. When the extraction region 702 is received by the region designation unit 516, the sorting unit 563 sorts the registered colors extracted from the extraction region 702 into the foreground group and the background group in accordance with the position of the radio button 712 being turned on. For example, the sorting unit 563 sorts the registered color extracted from the extraction region 702 into the foreground group, when the radio button 712 which is turned on when the extraction region 702 is received by the region designation unit 516 is the radio button 712 for the foreground group. Similarly, the sorting unit 563 sorts the registered color extracted from the extraction region 702 into the background group, when the radio button 712 which is turned on when the extraction region 702 is received by the region designation unit 516 is the radio button 712 for the background group. A check box 716 is a check box for enabling automatic selection of a neighboring color of the foreground color as the background color.

When the check box 716 is checked, the automatic region selection unit 517 extracts a color existing around the foreground color as the background color. For example, the automatic region selection unit 517 clusters the inside of the image of the workpiece 2 into the number of colors that has been designated in advance. The region designation unit 516 receives representative colors of some clusters among a plurality of generated clusters as the foreground colors designated by the user. In this case, the automatic region selection unit 517 decides a plurality of clusters having representative colors distant from the foreground colors in the color space as the background colors among representative colors of the remaining clusters that are not designated as the foreground colors, and selects (registers) the decided background colors. A confirm button 717 is a button to instruct confirmation of a color extraction result. A cancel button 718 is a button to discard the color extraction result.

In FIG. 7 and the like, an adjustment tab 720 is a tab configured to designate the coefficient (for example, the gain) and the like used to obtain the foreground-background image. An inspection tab 730 is a tab configured to display an image inspection result.

Distributions of Foreground Color and Background Color

Figure 10A:
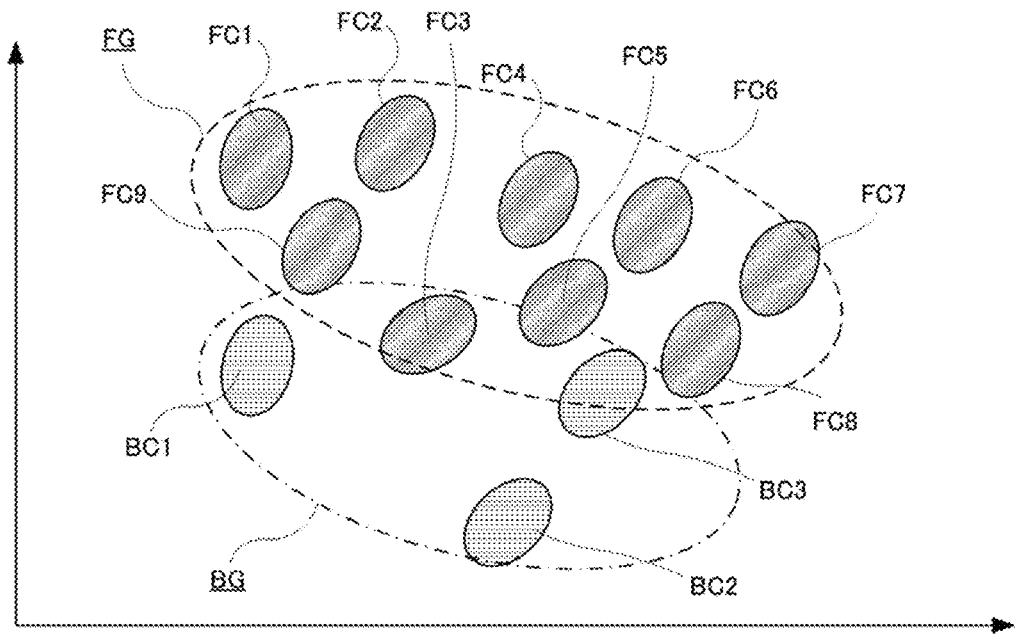
FIGS. 10A and 10B are views illustrating distributions of extracted colors in a color space.
Figure 10B:
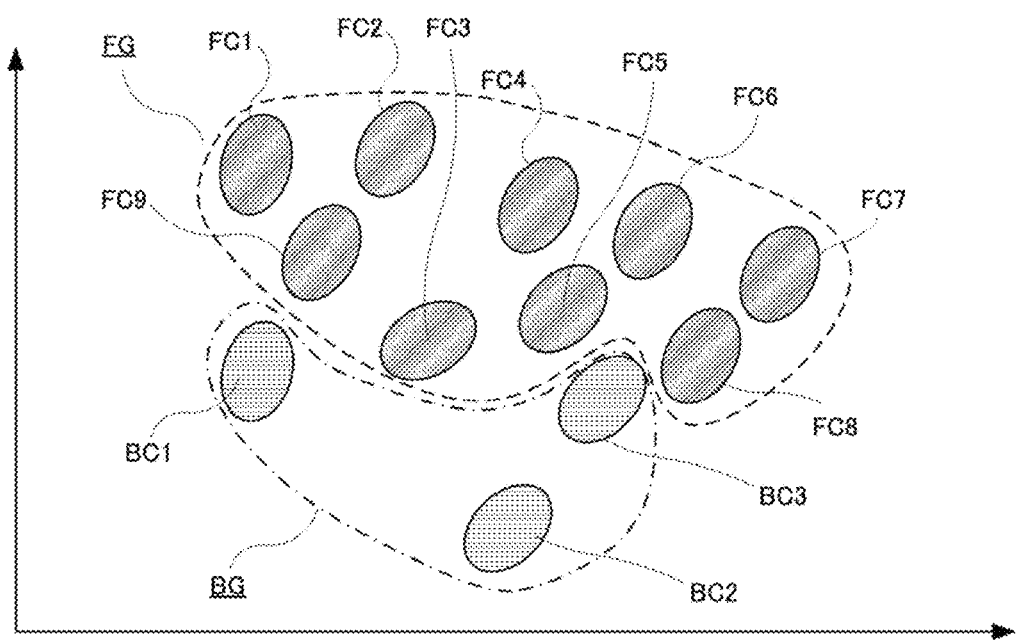

FIGS. 10A and 10B illustrate each distribution of foreground colors FC1 to FC9 that belongs to a foreground group FG and each distribution of background colors BC1 to BC3 that belongs to a background group BG. Here, the multi-dimensional color space is projected into a two-dimensional color space in order to simplify the description. The distribution of each color may be approximated to a normal distribution or the like. A color positioned at the center of the distribution of each color is the representative color (a position thereof is representative coordinates). Accordingly, a distance of each pixel of the color image with respect to the registered color is set by obtaining the Mahalanobis distance of each pixel of the color image with respect to the distribution of the registered color.

As illustrated in FIG. 10A, if there are only the distribution of the foreground group FG and the distribution of the background group BG, a boundary portion thereof greatly overlaps.

However, as the user registers each color information of the foreground colors FC1 to FC9 and each color information of the background colors BC1 to BC3, it is possible to more flexibly express the distribution of the foreground group FG and the distribution of the background group BG as illustrated in FIG. 10B. The work of registering the plurality of foreground colors forming the foreground group and the plurality of background colors forming the background group in this manner may be referred to as a sorting process or a grouping process.

Process of Creating Foreground-Background Image

Figure 11:
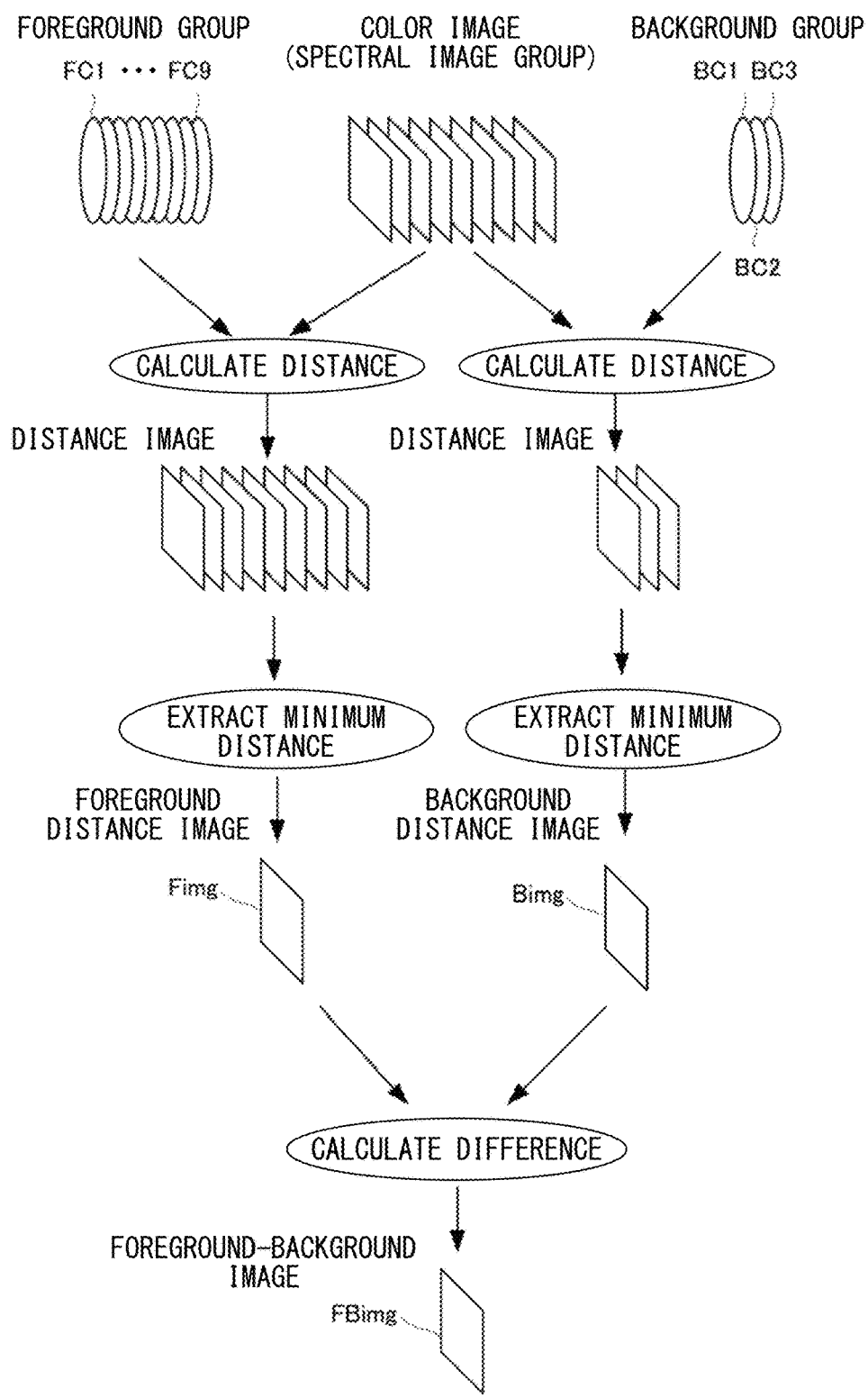
FIG. 11 is a view for describing a concept of a process of generation a foreground-background image.

FIG. 11 illustrates a process of creating a foreground-background image FBimg which is one type of inspection images. The inspection image generation unit 560 calculates the distance (Mahalanobis distance) between each of the foreground colors FC1 to FC9 that belongs to the foreground group FG and a color of each pixel of the color image of the workpiece 2, and creates nine distance images corresponding to the foreground colors FC1 to FC9. It is assumed that the color image is a multi-channel image, that is, constituted by a plurality of spectral images.

First, the distance image generation unit 564 of the inspection image generation unit 560 calculates a distance between the foreground color FC1 and a color of each pixel of the plurality of spectral images acquired for the workpiece 2, and creates one distance image corresponding to the foreground color FC1. Similarly, the distance image generation unit 564 calculates a distance between the foreground color FC2 and the color of each pixel of the plurality of spectral images acquired for the workpiece 2, and creates one distance image corresponding to the foreground color FC2. The distance image generation unit 564 also creates distance images for the remaining foreground colors FC3 to FC9, respectively. Further, the distance image generation unit 564 calculates the distance (Mahalanobis distance) between each of the background colors BC1 to BC3 that belongs to the background group BG and the color of each pixel of the plurality of spectral images acquired for the workpiece 2, and creates three distance images corresponding to the background colors BC1 to BC3. As described above, the value of each pixel constituting the distance image is the distance. In addition, the distance to the registered color such as the foreground color and the background color is a distance obtained using the representative color (center coordinates of distribution) in the distribution of the registered color as a reference.

The foreground image generation unit 565 of the inspection image generation unit 560 compares the nine distance images corresponding to the foreground colors FC1 to FC9 to obtain a minimum distance from among the nine distances for each coordinates, adopts the minimum distance as a representative distance of each coordinates, and creates a foreground distance image Fimg formed of the minimum distances. For example, a distance of coordinates (xi, yi) of interest is read out from the nine distance images, and the smallest distance among the read nine distances is adopted as a pixel value at the coordinates (xi, yi) of interest in the foreground distance image Fimg. Similarly, the background image generation unit 566 compares the three distance images corresponding to the background colors BC1 to BC3 to obtain a minimum distance from among the three distances for each coordinates, adopts the minimum distance as a representative distance of each coordinates, and creates a background distance image Bimg formed of the minimum distances.

The foreground-background image generation unit 567 of the inspection image generation unit 560 executes difference calculation between the foreground distance image Fimg and the background distance image Bimg to create the foreground-background image FBimg. For example, a pixel value G(xi, yi) at the coordinates (xi, yi) of interest in the foreground-background image FBimg is calculated from the following equation.

$$G(xi,yi)=g(db(xi,yi)-df(xi,yi))+Gmid \quad (1)$$

Here, g is a gain adjusted by the user in the adjustment tab 720. Further, db(xi, yi) is a pixel value at the coordinates (xi, yi) of interest in the background distance image Bimg. Further, df(xi, yi) is a pixel value at the coordinates (xi, yi) of interest in the foreground distance image Fimg. Gmid is an intermediate gradation. For example, if a maximum gradation is 255, Gmid is 128. However, Equation (1) is merely an example, and a value of Gmid may be zero.

Flowchart

Figure 12:
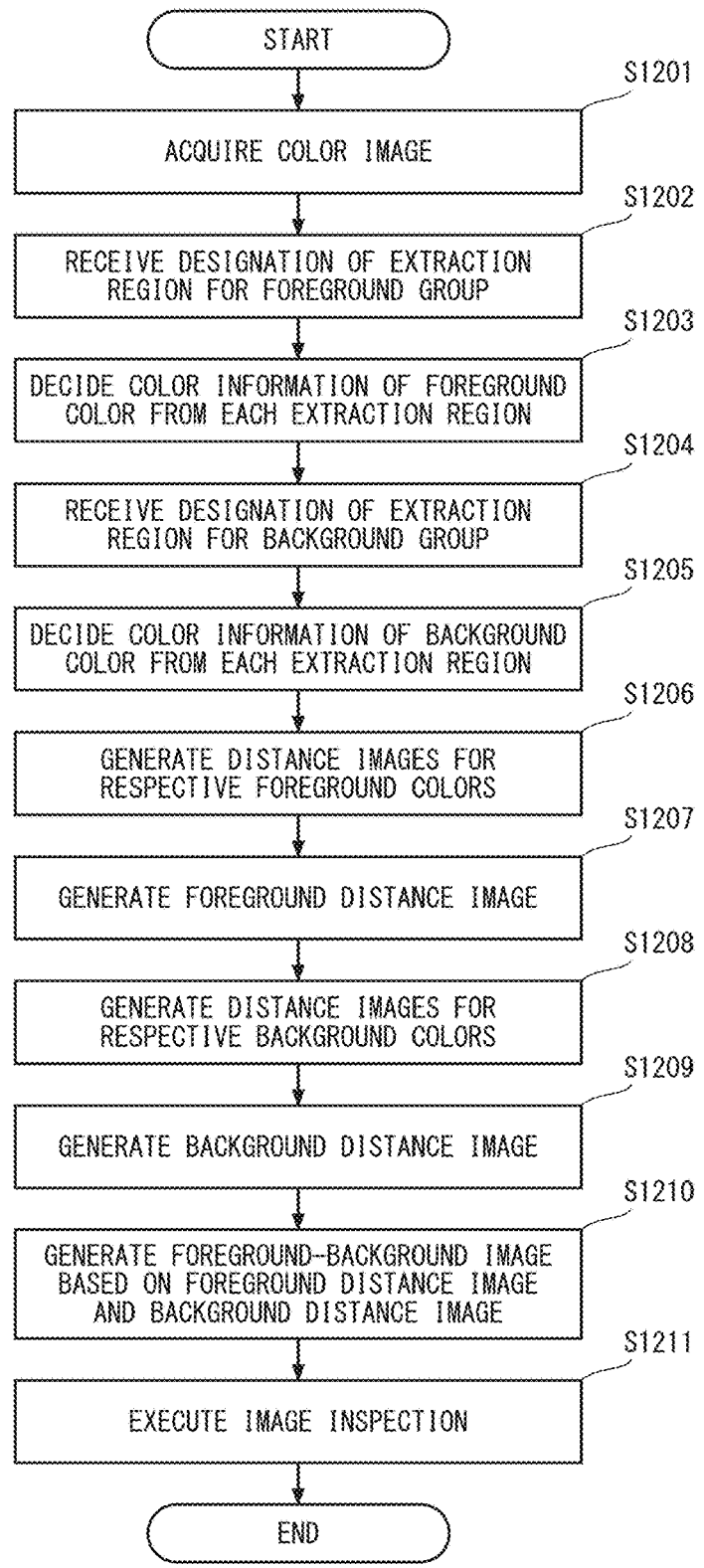
FIG. 12 is a flowchart illustrating image inspection.

FIG. 12 is a flowchart illustrating an image inspection method including a registered color extraction process and an inspection image creation process. The order of steps from S1202 to S1209 can be changed as long as there is no technical inconsistency.

In S1201, the processor 510 (the acquisition unit 561) acquires the color image of the workpiece 2 from the storage device 520 or the like.

In S1202, the processor 510 (the region designation unit 516) receives designation of the extraction region 702 from which the foreground color, which is to belong to the foreground group, is extracted. A position of the extraction region 702 in the color image and identification information of the group to which the extraction region 702 belongs are stored in the setting information 523.

In S1203, the processor 510 (the extraction unit 562) decides color information of each foreground color of the extraction region 702 designated by the user for the foreground group. The extraction unit 562 calculates the color information of the foreground color for each of the extraction regions 702 that belong to the foreground group. The color information includes the average pixel in the extraction region 702, the variance-covariance matrix, the number of pixels, and the like. When the nine extraction regions 702 are set for the foreground group, the extraction unit 562 decides the nine foreground colors FC1 to FC9. The color information of the foreground colors FC1 to FC9 is stored in the storage device 520 as the foreground color data 522.

In S1204, the processor 510 (the region designation unit 516) receives designation of the extraction region 702 from which the background color, which is to belong to the background group, is extracted. A position of the extraction region 702 in the color image and identification information of the group to which the extraction region 702 belongs are stored in the setting information 523.

In S1205, the processor 510 (the extraction unit 562) decides color information of each background color of the extraction region 702 designated by the user for the background group. The extraction unit 562 calculates the color information of the background color for each of the extraction regions 702 that belong to the background group. The color information includes the average pixel in the extraction region 702, the variance-covariance matrix, the number of pixels, and the like. When the three extraction regions 702 are set for the background group, the extraction unit 562 decides the three background colors BC1 to BC3. The color information of the background colors BC1 to BC9 is stored in the storage device 520 as the background color data 524.

In S1206, the processor 510 (the distance image generation unit 564) creates the distance image for each foreground color that belongs to the foreground group. The distance image generation unit 564 calculates the Mahalanobis distance between the coordinates of each pixel of the color image on the color space coordinates and the representative coordinates of the foreground color, and creates the distance image having the calculated distance as a pixel value. For example, the distance image generation unit 564 calculates the Mahalanobis distance between each pixel of the color image and the foreground color FC1, thereby replacing the value of each pixel in the color image with the Mahalanobis distance. As a result, the distance image for the foreground color FC1 is created. The distance image is generated for all the foreground colors that belongs to the foreground group.

In S1207, the processor 510 (the foreground image generation unit 565) combines the distance images for the foreground group to create the foreground distance image (foreground image) Fimg. For example, the foreground image generation unit 565 compares the plurality of range images that belongs to the foreground group, and selects the minimum pixel value in each coordinates as the pixel value of each coordinates in the foreground distance image Fimg. For example, when the pixel value (distance) of the foreground color FC1 is smaller than each pixel value of the other foreground colors FC2 to FC9 for a pixel at coordinates (x, y), the pixel value of the foreground color FC1 is selected as a pixel value of the pixel at the coordinates (x, y) in the foreground distance image Fimg. As this selection process is executed for all the coordinates (pixels), the foreground distance image Fimg is completed. The foreground distance image Fimg is stored in the storage device 520 as the foreground image data 525.

In S1208, the processor 510 (the distance image generation unit 564) creates the distance image for each background color that belongs to the background group. The distance image generation unit 564 calculates the Mahalanobis distance between the coordinates of each pixel of the color image on the color space coordinates and the representative coordinates of the background color, and creates the distance image having the calculated distance as a pixel value. For example, the distance image generation unit 564 calculates the Mahalanobis distance between each pixel of the color image and the background color BC1, thereby replacing the value of each pixel in the color image with the Mahalanobis distance. As a result, the distance image for the background color BC1 is created. The distance image is generated for all the background colors that belongs to the background group.

In S1209, the processor 510 (the background image generation unit 566) combines the distance images for the background group to create the background distance image (background image) Bimg. For example, the background image generation unit 566 compares the plurality of distance images that belongs to the background group, and selects the minimum pixel value in each coordinates as the pixel value of each coordinates in the background distance image Bimg. For example, when the pixel value (distance) of the background color BC1 is smaller than each pixel value of the other background colors BC2 and BC3 for a pixel at coordinates (1, 1), the pixel value of the background color BC1 is selected as a pixel value of the pixel at the coordinates (x, y) in the background distance image Bimg. As this selection process is executed for all the coordinates (pixels), the background distance image Bimg is completed. The background distance image Bimg is stored in the storage device 520 as the background image data 526. When there is only one background color, a distance image thereof is adopted directly as the background distance image Bimg.

In S1210, the processor 510 (the foreground-background image generation unit 567) obtains the difference image between the foreground distance image Fimg and the background distance image Bimg, thereby creating the foreground-background image. For example, the foreground-background image is created using Equation (1). The foreground-background image is held in the storage device 520 as the inspection image data 527.

In S1211, the processor 510 executes image inspection using the foreground-background image. The processor 510 instructs the inspection unit 531 to execute predetermined image inspection on the foreground-background image. The inspection unit 531 reads the inspection image data 527 of the foreground-background image from the storage device 520 and executes the image inspection using the inspection tool designated by the user. For example, the inspection unit 531 extracts an edge of an inspection target part from the foreground-background image to measure a dimension of the inspection target part, and performs binarization processing to calculate the area thereof. The determination unit 540 compares the inspection result acquired by the inspection unit 531 with a threshold (a tolerance or the like), and determines whether the workpiece 2 is a passed product.

Figure 13:
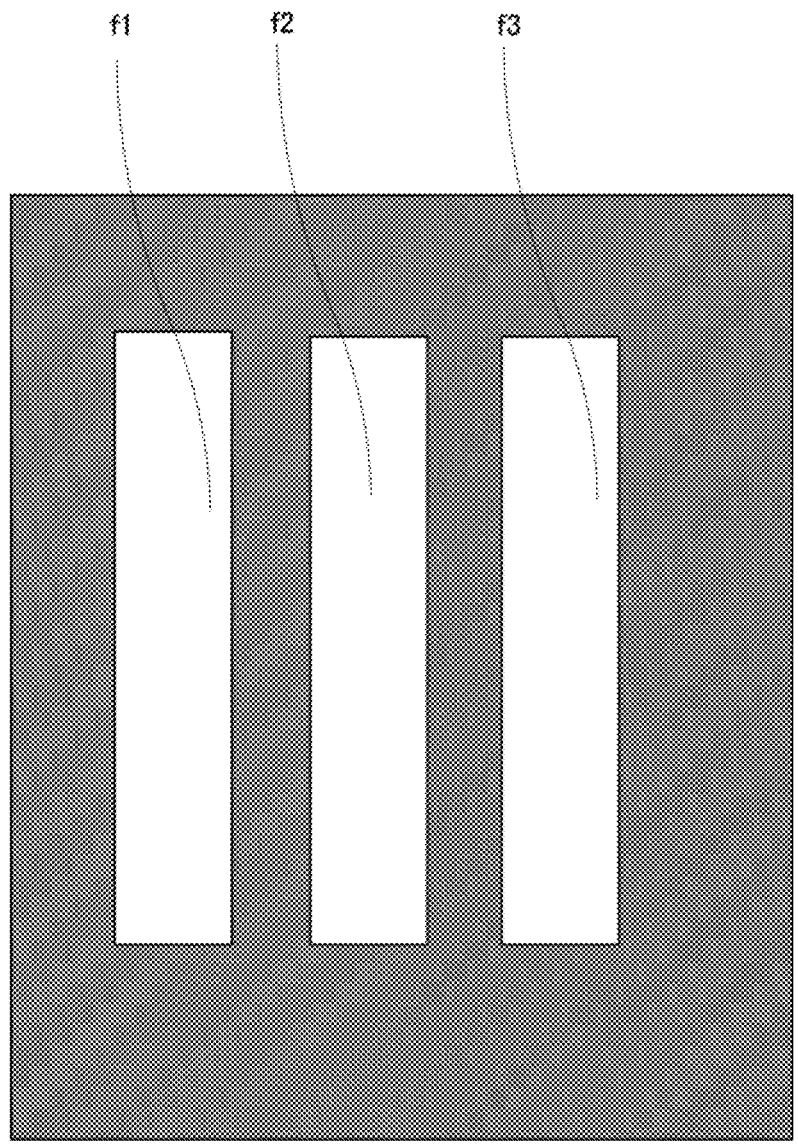
FIG. 13 is a view illustrating an example of the foreground-background image.

FIG. 13 illustrates an example of the foreground-background image FBimg. The cables f1, f2, and f3 have mutually different colors, but are extracted from the background as the foreground to be distinguished from each other. As a result, it is possible to accurately measure dimensions of the cables f1, f2, and f3.

SUMMARY

The acquisition unit 561, the camera 4, and the like are examples of an acquisition unit which acquires a color image having the inspection target object as the foreground and the surroundings of the inspection target object as the background, the color image in which each pixel has multi-dimensional color information. In particular, the acquisition unit 561, the camera 4, and the like are examples of the acquisition unit which acquires the color image of the inspection target object, the color image including the plurality of spectral images. The display unit 7 is an example of a display unit which displays the color image acquired by the acquisition unit 561. The region designation unit 516 is an example of a region designation unit which receives designation of a region including a plurality of pixels in the color image displayed on the display unit 7. In particular, the region designation unit 516 receives designation of a plurality of foreground regions including one or a plurality of pixels in the color image displayed on the display unit 7. When color information is extracted by a dropper, the region may be constituted by one pixel. The designation of the background region is optional. The extraction unit 562 is an example of an extraction unit which extracts color information of each region designated by the region designation unit 516. In particular, the extraction unit 562 extracts color information including the color distribution in each of the plurality of foreground regions designated by the region designation unit 516 and the color information including the color distribution in the background region distinguished from the plurality of foreground regions. Further, the extraction unit 562 registers the color information extracted from each of the plurality of foreground regions as the foreground color, and registers the color information extracted from the background region as the background color. The plurality of foreground colors forms the foreground group, and one or a plurality of the background colors form the background group. The foreground image generation unit 565 calculates the distance between the color of each pixel of the plurality of spectral images and each of the plurality of foreground colors on the color space coordinates, generates the plurality of distance images having the distance as the pixel value, and generates the foreground distance image based on the plurality of distance images. The distance image generation unit 564 may perform this generation of the distance image. The background image generation unit 566 calculates the distance on the color space coordinates between the color of each pixel of the plurality of spectral images and the background color, generates the distance images having the distance as the pixel value, and generates the background distance image based on the plurality of generated distance images. The distance image generation unit 564 may perform this generation of the distance image. The inspection unit 531 is an example of an inspection unit which inspects the inspection target object using the difference image between the foreground distance image and the background distance image. In this manner, it is possible to easily extract the foreground color or the background color as the extracted color by designating at least the foreground region by the user according to the present embodiment. Accordingly, the burden on the user relating to the designation of the extracted color may be alleviated, and the variation in the result of the image inspection may be also reduced. In addition, it is possible to easily define the plurality of foreground colors forming the foreground group and at least one background color forming the background group by setting a region forming each of the groups while viewing the color image of the inspection target object. Thus, it is possible to stably extract the color of each foreground region even in the case where the plurality of foreground regions exists.

As described with reference to FIG. 11, the foreground image generation unit 565 may include a selection section which compares the plurality of distance images generated for the plurality of foreground colors, and selects the minimum pixel value in each pixel as the pixel value of each coordinates in the foreground distance image, or may function as the selection section. The selection section can be implemented as a function of searching the above-described minimum distance. When a plurality of foregrounds exists, a pixel having a color close to any of the foreground colors is extracted as a foreground. As illustrated in FIG. 9, in the case where the three cables f1, f2, and f3, which are red, green, and blue, respectively, exist, a color close to any one of the nine foreground colors in the color image is likely to be separated as a foreground in the foreground distance image. For example, seafood such as shrimps seems to have the same color at first glance, but actually each of the shrimps has different colors. In the image inspection, however, it is necessary to separate a plurality of shrimps having slightly different colors from a background as similar shrimps. Therefore, it is possible to separate the plurality of shrimps, which is the foreground in the foreground-background image, from the background by setting the extraction region 702 for the shrimps having various colors and extracting a plurality of foreground colors to form the foreground group.

As illustrated in FIGS. 7 to 9, the region designation unit 516 may receive designation of the background region in the color image. The region designation unit 516 may receive designation of a plurality of background regions from which the background colors are extracted, respectively. Similarly, the region designation unit 516 may receive designation of a plurality of foreground regions from which the foreground colors are extracted, respectively.

The region designation unit 516 may include a decision unit which decides, in the color image, the region including the color close to any of the plurality of foreground colors on the color space as the background region. The above-described automatic region selection unit 517 is an example of the decision unit. The automatic region selection unit 517 may be implemented as one function of the region designation unit 516. That is, when the check box 716 is checked, the region designation unit 516 may cause the automatic region selection unit 517 to decide the extraction region 702 for extraction of the background color and display a frame line indicating the decided extraction region 702 in the image display region 701. Thus, the burden of the user to designate the extraction region 702 for extraction of the background color is alleviated.

The background image generation unit 566 calculates the distance between the coordinates of each pixel of the image on the color space coordinates and the representative coordinates of each of the plurality of pieces of color information that belongs to the background group, generates the distance image having the distance as the pixel value for each of the plurality of color information, and generates the background image based on the plurality of generated distance images. In this manner, the plurality of background colors may belong to the background group. There is a case where the background color is constituted not by one color but by various colors in the workpiece 2. For example, when a shrimp as the foreground is separated from a dried noodle and seaweed as backgrounds in instant food, it is necessary to extract a color of the dried noodle and a color of the seaweed. In such a case, it may be advantageous to extract a plurality of background colors, generate a plurality of distance images, and generate a single background distance image using the plurality of distance images.

The background image generation unit 566 may include a selection section which compares the plurality of distance images generated for the plurality of background colors, and selects the minimum pixel value in each pixel as the pixel value of each pixel in the background distance image, or may function as the selection section. As a result, a color close to any of the plurality of background colors existing in the color image will be separated as the background color. For example, the other part of the dried noodle having a color close to the background color extracted from a part of the dried noodles is extracted as the background. In addition, a color of the other seaweed having a color close to the background color extracted from a part of the seaweed is also extracted as the background. As a result, it is easy to separate the shrimp as the foreground and the dried noodle and seaweed as the backgrounds using color information.

Although the foreground group and background group are exemplified in the above-described embodiment, the number of groups may be three or more. The region designation unit 516 receives designation of a first region including a plurality of pixels in the color image displayed on the display unit 7. The region designation unit 516 may receive designation of a second region including a plurality of pixels in the color image displayed on the display unit 7.

In addition, similar to the foreground region and the background region, the second region may be automatically decided based on the first region. The extraction unit 562 extracts color information including a color distribution in the first region designated by the region designation unit 516 and color information including a color distribution in the second region that is distinguished from the first region, and registers the extracted color information as a first registered color which is a registered color for the first region and a second registered color which is a registered color for the second region. The distance image generation unit 564, the foreground image generation unit 565, and the background image generation unit 566 are examples of an image generation unit. That is, the image generation unit calculates a distance between a color of each pixel in a plurality of spectral images and the first registered color on color space coordinates, generates a plurality of distance images having the distance as a pixel value, and generates a first distance image based on the plurality of generated distance images, and calculates a distance between the color of each pixel in the plurality of spectral images and the second registered color on the color space coordinates, generates a distance image having the distance as a pixel value, and generates a second distance image based on the plurality of generated distance images. The inspection unit 531 inspects an inspection target object using a combined image of the first distance image and the second distance image.

The region designation unit 516 may receive designation of a plurality of third regions including a plurality of pixels in the color image displayed on the display unit 7. In this case, the extraction unit 562 extracts color information including a color distribution in the third region designated by the region designation unit 516, and registers the extracted color information as a third registered color which is a registered color for the third region. The image generation unit calculates a distance on the color space coordinates between the color of each pixel in the plurality of spectral images and the third registered color, generates a plurality of distance images having the distance as a pixel value, and generates a third distance image based on the plurality of generated distance images. Further, the image generation unit may generate a combined image by combining the first distance image, the second distance image, and the third distance image. The inspection unit 531 inspects the inspection target object using the combined image of the first distance image, the second distance image, and the third distance image. In this manner, it is possible to apply the present embodiment even when the first group including one or more first regions, the second group including one or more second regions, and the third group including one or more third regions are formed.

A combining method can be implemented by creating an index image in which an ID of a group adopted as gradation of a minimum distance image is a pixel value. First, zero is set to the gradation of each pixel constituting the index image. The color group ID is assigned from one. The ID of the group to which a pixel of the distance image belongs is substituted as the gradation of that pixel. When the gradation of the distance image is the largest in any group of the distance images, the gradation of the index image is maintained at zero, which is a pixel that does not belong to any group.

The UI 700 illustrated in FIG. 7 or the like is merely an example. For example, the UI 700 may include a foreground color extraction button to instruct extraction of the foreground color and a background color extraction button to instruct extraction of the background color. When detecting the operation of the foreground color extraction button or the background color extraction button, the UI management unit 514 may display a dropper as an object for color extraction. The extraction unit 562 extracts color information of the extraction region 702 (one pixel) designated by the dropper. The foreground color and the background color may be extracted in this manner. In addition, when these buttons are pressed, the above-described color clustering may be applied to select the foreground color or the background color.

The following method may be adopted as automatic selection of the background color. When selection of the foreground color is completed, the MSI processing unit 511 or the like executes a clustering process on colors within a measurement region or the entire image. A color distant from all the foreground colors is selected as the background color.

In this manner, the color apparently distant from the foreground color will be selected as the background color.

A background color which is a neighboring color of the foreground color may be selected as a comparison color. This may be advantageous at the time of individually performing color adjustment of the foreground color. For example, with respect to the foreground color, which is to be individually adjusted, selected from the plurality of foreground colors, a color which is closest to a foreground color on the color space may be selected from the plurality of background colors as the comparison color and displayed on the display unit 7.

Figure 17:
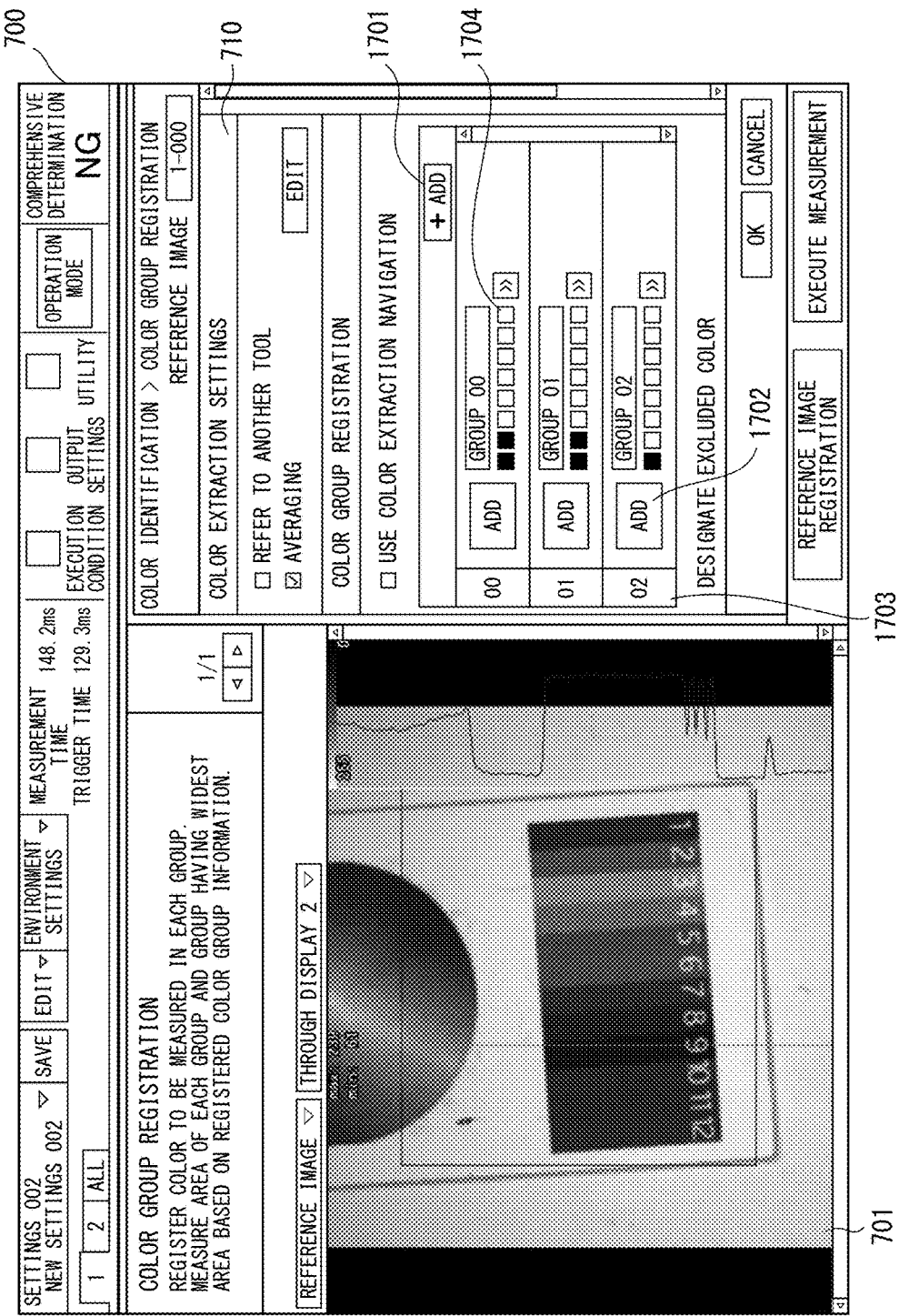
FIG. 17 is a view illustrating a UI that assists designation of an extracted color.

FIG. 17 illustrates another example of the UI 700. In this example, it is assumed that one or more measurement target colors are registered in each of three or more groups. When detecting that a group addition button 1701 has been pressed, the UI management unit 514 adds a group. In this example, there are three groups since the group addition button 1701 has been pressed three times. A color addition button 1702 is pressed at the time of adding a registered color to each group. When the color addition button 1702 of any group is pressed, the UI management unit 514 activates a dropper tool, extracts a color of a region designated by the user from the image of the workpiece displayed on the image display region 701, and registers the extracted color to a group selected by the user. In this example, two colors are registered in each of groups 00 and 01. One color is registered in group 02. In an index color display unit 1703, index colors of the respective groups are displayed.

Figure 18:
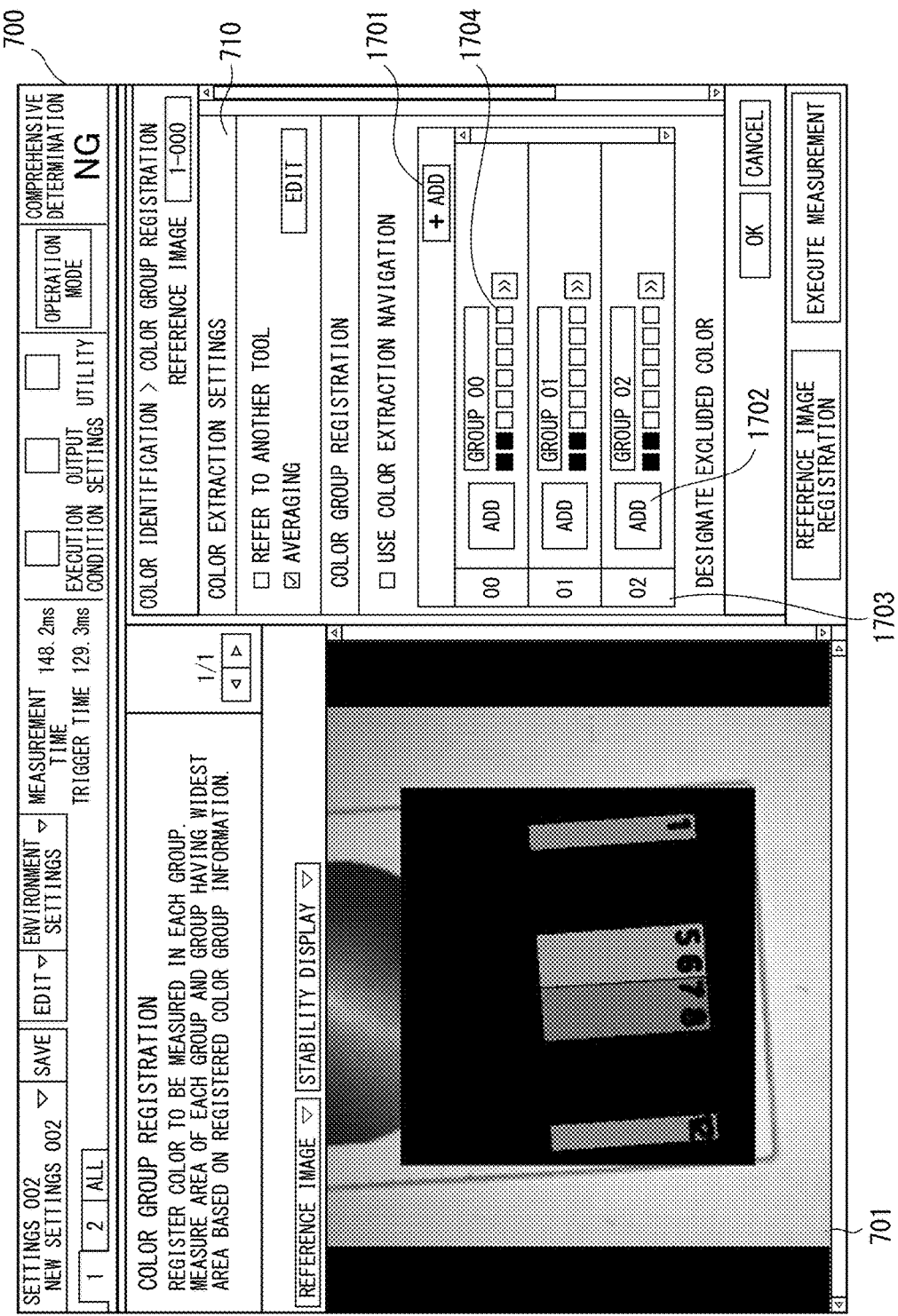
FIG. 18 is a view illustrating a UI that assists designation of an extracted color.

FIG. 18 is a view illustrating an example of a color extraction result. In this example, clustering is applied to an image within a designation region designated by the user in the image of the workpiece, and a color extraction image is generated and displayed in the image display region 701. The inspection image generation unit 560 specifies one group by determining which group of colors the color of each pixel constituting the image in the designation region is close to. For example, the inspection image generation unit 560 calculates which representative color among representative colors of the respective groups the color of each pixel constituting the image in the designation region is close to. The inspection image generation unit 560 generates the color extraction result (inspection image) by replacing the color of each pixel constituting the image in the designation region with an index color of the specified group. The inspection image generation unit 560 may replace a pixel value with zero for a color distant from any group such that the color is not sorted into any group. In FIG. 18, color regions 1 and 12 are replaced with the index color of the group 02. The color regions 7 and 8 are replaced with the index color of the group 00. The color regions 5 and 6 are replaced with the index color of the group 01.

Figure 19:
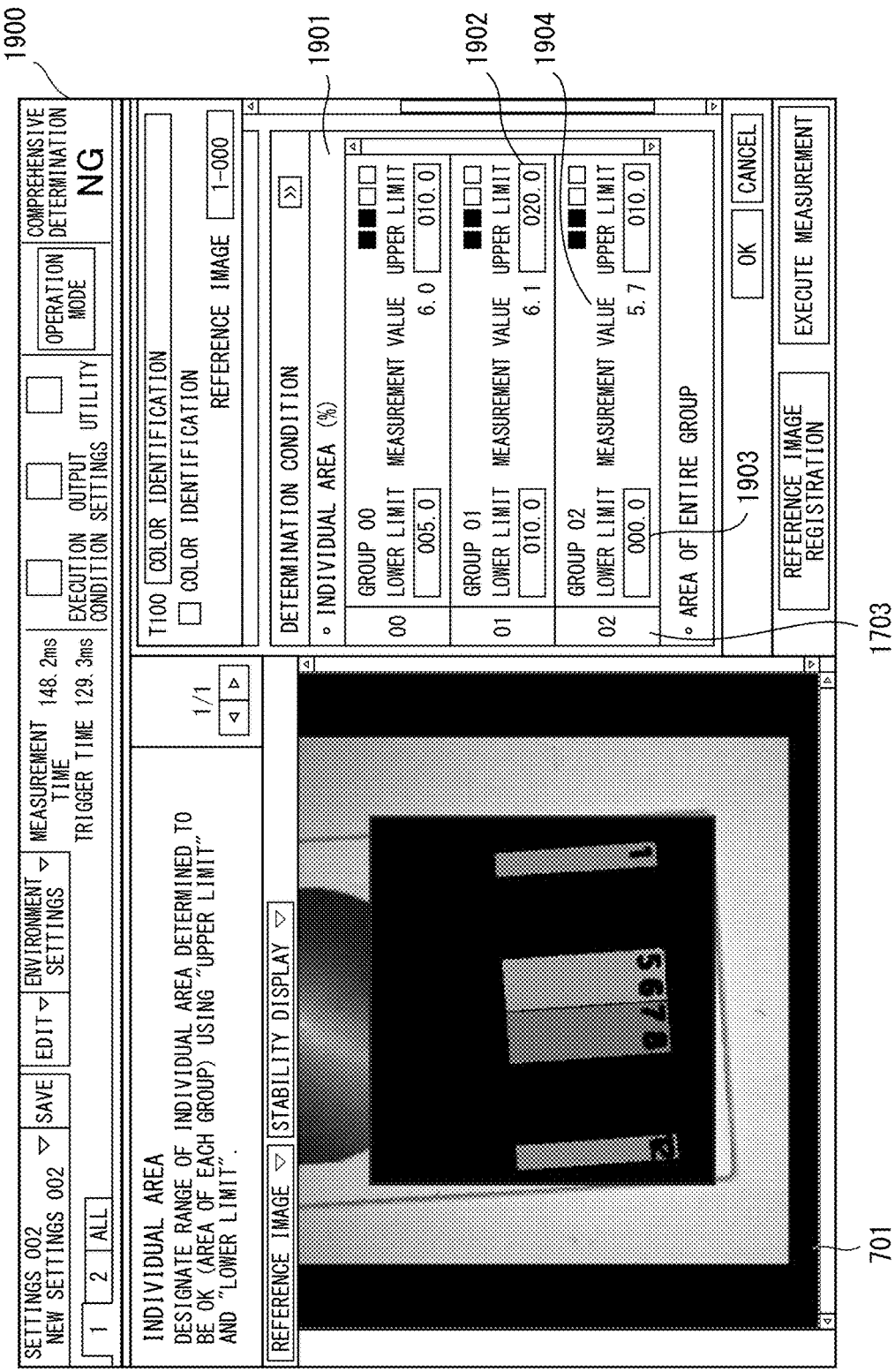
FIG. 19 is a view illustrating a UI that assists designation of an extracted color.

FIG. 19 illustrates a UI 1900 configured to execute inspection setting. The UI management unit 514 may receive the inspection setting for the inspection image through the UI 1900. In this example, inspection is made on whether a measurement value of the area of a region classified into each color satisfies a tolerance. A determination condition setting unit 1901 is provided with a lower limit value input unit 1903 which receives an input of a lower limit value of the tolerance for each of the plurality of groups, an upper limit value input unit 1902 which receives an input of an upper limit value of the tolerance, and a measurement value display unit 1904 which displays the measurement value of the area where the inspection image has been measured. The UI management unit 514 stores inspection settings set through the determination condition setting unit 1901 in the setting information 523. The inspection unit 531 obtains the measurement values of the respective groups. For example, in the case of the group 02, the inspection unit 531 counts each area of the regions 1 and 12 to obtain the measurement value. The UI management unit 514 receives this measurement value and displays the measurement value on the measurement value display unit 1904.

Figure 20:
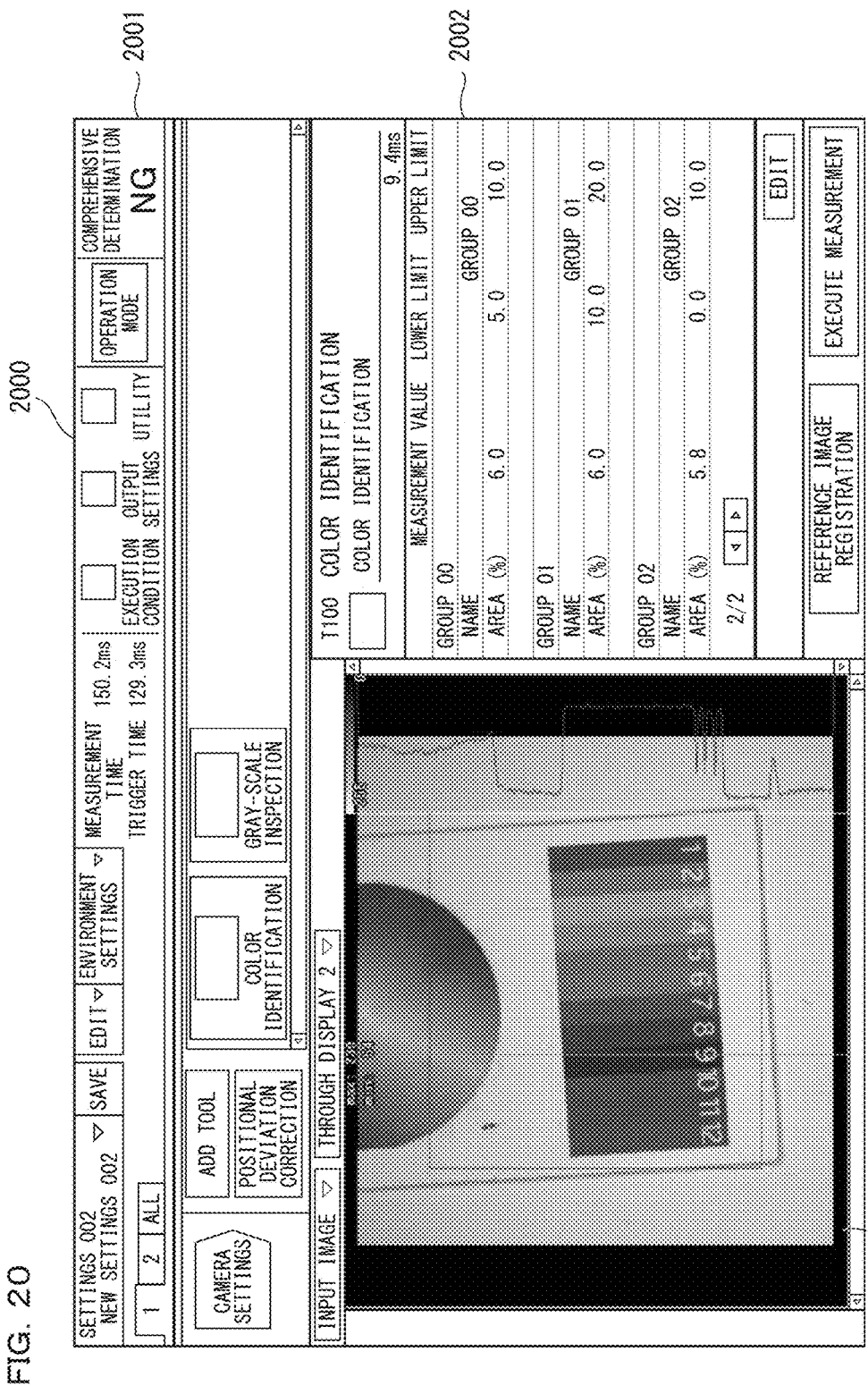
FIG. 20 is a view illustrating a UI that assists designation of an extracted color.
Figure 21:
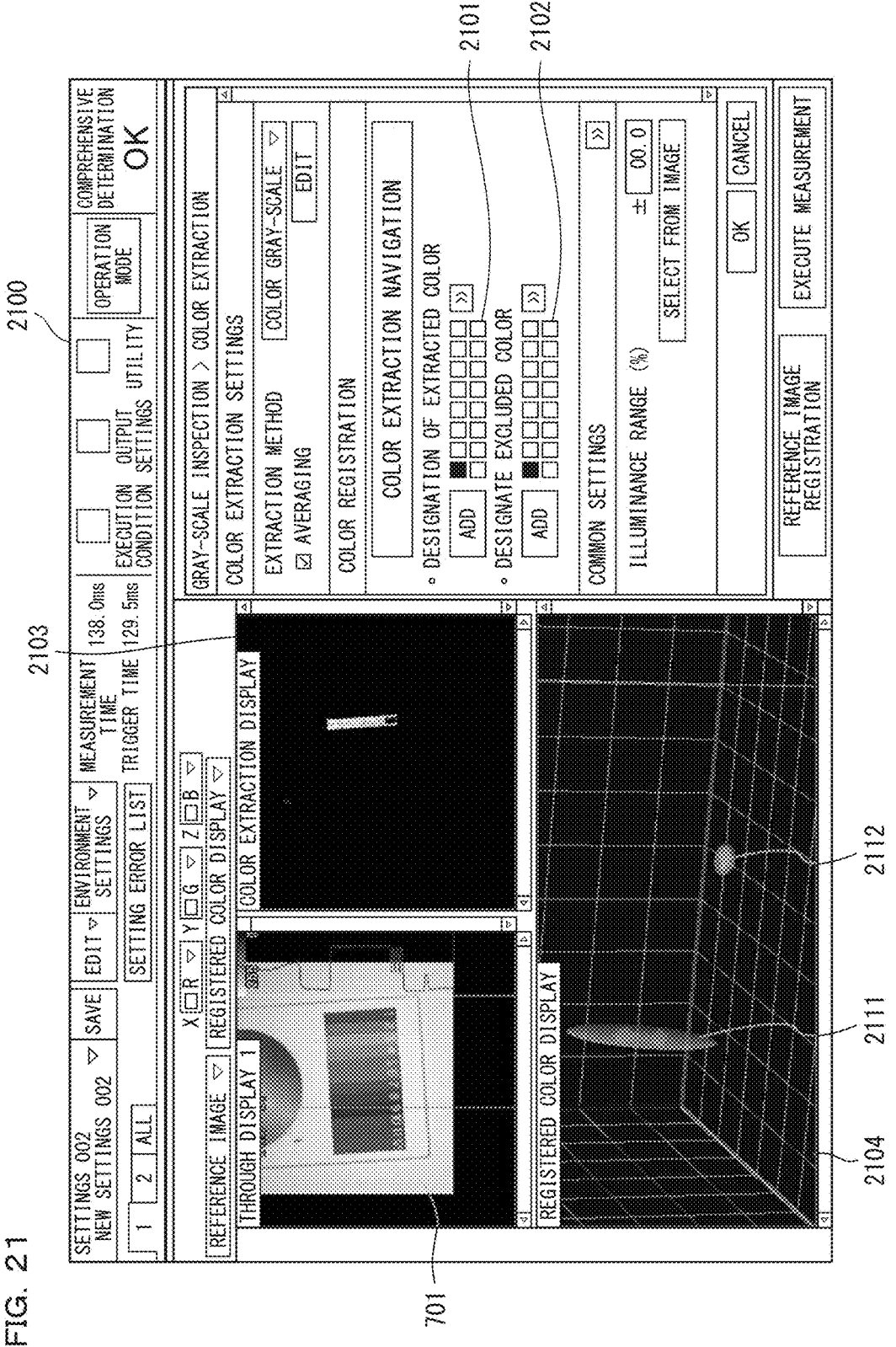
FIG. 21 is a view illustrating a UI that assists designation of an extracted color.

FIG. 20 illustrates an example of a UI 2000 illustrating an inspection result. A determination result display unit 2001 displays "OK" if all the measurement values of the three groups are within the tolerance. On the other hand, the determination result display unit 2001 displays "NG" if the measurement value of one of the three groups is outside the tolerance. In this example, the measurement result of the group 01 is out of the tolerance although the measurement values of the groups 00 and 02 are within the tolerance. Thus, the determination unit 540 decides the overall determination as fail. FIG. 21 illustrates an example of a UI 2100 for extraction and setting of a foreground and a background. A color designation unit 2101 is a UI for registration of the foreground color. A color designation unit 2102 is a UI for registration of the background color (exclusion color). The foreground color and the background color are extracted from the image of the workpiece displayed in the image display region 701 and registered. An inspection image display unit 2103 displays a difference image between a foreground image obtained from the foreground color and a background image obtained from the background color. A separation degree display unit 2104 is a three-dimensional graph that indicates a degree of separation between the foreground color and the background color in the color space. A color distribution 2111 indicates a color distribution of the foreground color. A color distribution 2112 indicates a color distribution of the background color. In this example, the color distribution of the foreground color and the color distribution of the background color are sufficiently distant from each other, and thus, the region (region 3) of the inspection target color in the inspection image is clearly separated from the background. That is, the user can understand that the foreground color and the background color are accurately registered by viewing the three-dimensional graph.

What is claimed is:
1. An image inspection device comprising:
an acquisition unit which acquires a color image of an inspection target object, the color image including a plurality of spectral images;
a display unit which displays the color image acquired by the acquisition unit;
a region designation unit which receives designation of a plurality of foreground regions including a plurality of pixels in the color image displayed on the display unit;
an extraction unit which extracts color information including a color distribution in each of the plurality of foreground regions designated by the region designation unit and color information including a color distribution in a background region distinguished from the plurality of foreground regions and registers the extracted color information as foreground colors for the plurality of foreground regions, respectively, and a background color for the background region;
a foreground image generation unit which calculates a distance on color space coordinates between a color of each pixel in the plurality of spectral images and each of the plurality of foreground colors, generates a plurality of distance images having the distance as a pixel value, and generates a foreground distance image based on the plurality of generated distance images;

a background image generation unit which calculates a distance on the color space coordinates between the color of each of the pixels in the plurality of spectral images and the background color, generates a distance image having the distance as a pixel value, and generates a background distance image based on the plurality of generated distance images; and an inspection unit which inspects the inspection target object using a foreground-background image which is a difference image between the foreground distance image and the background distance image.

2. The image inspection device according to claim 1, wherein
the foreground image generation unit includes a selection section which compares the plurality of distance images generated for the plurality of foreground colors, and selects a minimum pixel value in each pixel as a pixel value of each coordinates in the foreground distance image.

3. The image inspection device according to claim 1, wherein
the region designation unit receives designation of the background region in the color image.

4. The image inspection device according to claim 1, wherein
the region designation unit includes a decision unit which decides, in the color image, a region including a color which is distant from any of the plurality of foreground colors on a color space as the background region.

5. The image inspection device according to claim 1, wherein
the background image generation unit includes a selection section which compares the plurality of distance images generated for a plurality of the background colors, and selects a minimum pixel value in each pixel as a pixel value of each pixel in the background distance image.

6. The image inspection device according to claim 5, wherein
the region designation unit is configured to receive designation of a plurality of background regions from which the plurality of background colors are extracted.

7. An image inspection device comprising:
an acquisition unit which acquires a color image of an inspection target object, the color image including a plurality of spectral images;
a display unit which displays the color image acquired by the acquisition unit;
a region designation unit which receives designation of a first region including a plurality of pixels in the color image displayed on the display unit;
an extraction unit which extracts color information including a color distribution in the first region designated by the region designation unit and color information including a color distribution in a second region distinguished from the first region, and registers the extracted color information as a first registered color which is a registered color for the first region and a second registered color which is a registered color for the second region;
an image generation unit which calculates a distance between a color of each pixel in the plurality of spectral images and the first registered color on color space coordinates, generates a plurality of distance images having the distance as a pixel value, and generates a first distance image based on the plurality of generated distance images, and calculates a distance between the color of each of the pixels in the plurality of spectral images and the second registered color on the color space coordinates, generates a distance image having the distance as a pixel value, and generates a second distance image based on the plurality of generated distance images; and an inspection unit which inspects the inspection target object using a combined image of the first distance image and the second distance image.

8. The image inspection device according to claim 7, wherein
the region designation unit receives designation of a plurality of third regions including a plurality of pixels in the color image displayed on the display unit,
the extraction unit extracts color information including a color distribution in the third region designated by the region designation unit and registers the extracted color information as a third registered color which is a registered color for the third region,
the image generation unit calculates a distance on the color space coordinates between the color of each of the pixels in the plurality of spectral images and the third registered color, generates a plurality of distance images having the distance as a pixel value, and generates a third distance image based on the plurality of generated distance images, and
the inspection unit inspects the inspection target object using a combined image of the first distance image, the second distance image, and the third distance image.

9. An image inspection device comprising:
an acquisition unit which acquires a color image of an inspection target object, the color image including a plurality of spectral images;
a display unit which displays the color image acquired by the acquisition unit;
an extraction unit which extracts color information including a color distribution in each of a plurality of foreground regions in the color image and color information including a color distribution in a background region distinguished from the plurality of foreground regions and registers the extracted color information as foreground colors for the plurality of foreground regions, respectively, and a background color for the background region;
a foreground image generation unit which calculates a distance on color space coordinates between a color of each pixel in the plurality of spectral images and each of the plurality of foreground colors, generates a plurality of distance images having the distance as a pixel value, and generates a foreground distance image based on the plurality of generated distance images;
a background image generation unit which calculates a distance on the color space coordinates between the color of each of the pixels in the plurality of spectral images and the background color, generates a distance image having the distance as a pixel value, and generates a background distance image based on the plurality of generated distance images; and
an inspection unit which inspects the inspection target object using a foreground-background image which is a difference image between the foreground distance image and the background distance image.

* * * * *